(12) United States Patent
Janda et al.

(10) Patent No.: US 6,849,398 B1
(45) Date of Patent: Feb. 1, 2005

(54) USE OF ENCODED REACTION CASSETTE

(75) Inventors: Kim D. Janda, San Diego, CA (US); Richard A. Lerner, La Jolla, CA (US); Hicham Fenniri, West Lafayette, IN (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 08/716,448

(22) PCT Filed: Jan. 18, 1996

(86) PCT No.: PCT/US96/00888

§ 371 (c)(1),
(2), (4) Date: May 22, 1998

(87) PCT Pub. No.: WO96/22391

PCT Pub. Date: Jul. 25, 1996

(51) Int. Cl.$^7$ .......................... C12Q 1/68; C12P 19/34; C12M 1/34; C07H 21/02
(52) U.S. Cl. ........................ 435/6; 435/183; 435/287.2; 536/23.1
(58) Field of Search .......................... 435/6, 91.1, 91.2, 435/183, 194, 287.2; 536/23.1, 24.3, 24.33; 530/350

(56) References Cited

U.S. PATENT DOCUMENTS

| | | | |
|---|---|---|---|
| 4,272,506 A | 6/1981 | Schwarzberg | |
| 5,190,864 A | 3/1993 | Giese et al. | |
| 5,200,314 A | 4/1993 | Urdea | |
| 5,318,897 A | 6/1994 | Paul | |
| 5,380,833 A | 1/1995 | Urdea | |
| 5,432,062 A | 7/1995 | Turecek | |
| 5,462,852 A | 10/1995 | Arthur et al. | |
| 5,559,000 A | * 9/1996 | Janda et al. | ............ 435/6 |

OTHER PUBLICATIONS

Kahne, et al., "Hydrolysis of a Peptide Bond in Neutral Water", *J. Am. Chem. Soc. 110*: 7529–7534 (1988).
D'Aquila, et al., "Maximizing Sensitivity and Specificity of PCR by Preamplification Heating", *Nucleic Acids Research 19*: 3749 (1991).
Gao, et al., "H–Phosphonate Oligonucleotide Synthesis on a Polyethylene Glycol/Polystyrene Copolymer", *Tetrahedron Lett. 32*: 5477–5480 (1991).
Lewis, et al., "Medium Effects in Antibody–Catalyzed Reactions", *Science 253*: 1019–1022 (1991).
Bertozzi, et al., "The Synthesis of Heterobifunctional Linkers for the Conjugation of Ligands to Molecular Probes", *J. Org. Chem. 56*: 4326–4329 (1991).
Gong, et al., "A Chromogenic Assay for Screening Large Antibody Libraries", *J. Am. Chem. Soc. 114*: 1486–1487 (1992).
Sano, et al., "Immuno–PCR: Very Sensitive Antigen Detection by Means of Specific Antibody–DNA Conjugates", *Science 258*: 120–122 (1992).
Sano, et al., "Immuno–PCR with a Commercially Available Avidin System", *Science 260*: 698–699 (1993).
Lane, et al., "Sensitive Detection of Catalytic Species without Chromophoric Substrates", *J. Am. Chem. Soc. 115*: 2078–2080 (1993).
Nielsen, et al., "Synthetic Methods for the Implimentation of Encoded Combinatorial Chemistry", *J. Am. Chem. Soc. 115*: 9812–9813 (1993).
Mirzabekov, et al., "DNA Sequencing by Hybridization –a Megasequencing Method and a Diagnostic Tool?", *TIBTECH 12*: 27–32 (1994).
Meldal, et al., "Portion–Mixing Peptide Libraries of Quenched Fluorogenic Substrates for Complete Subsite Mapping of Endoprotease Specificity" *Proc. Natl. Acad. Sci. USA 91*: 3314–3318 (1994).
de la Torre, et al., "Stepwise Solid–Phase Synthesis of Oligonucleotide–Peptide Hybrids", *Tetrahedron Lett. 35*: 2733–2736 (1994).
Nielsen, et al., "Toward Chemical Implementation of Encoded Combinatorial Libraries", *Methods 6*: 361–371 (1994).
Ogura, et al., "Use of the Fluorescent Dye YOYO–1 to Quantify Oligonucleotides Immobilized on Plastic Plates", *BioTechniques 16*: 1032–1033 (1994).
Janda, "Tagged Versus Untagged Libraries: Methods for the Generation and Screening of Combinatorial Chemical Libraries", *Proc. Natl., Acad. Sci. USA 91*: 10779–10785 (1994).

* cited by examiner

Primary Examiner—Bradley L. Sisson
(74) *Attorney, Agent, or Firm*—Donald G. Lewis; Thomas Fitting

(57) ABSTRACT

A reaction cassette has been designed for the highly sensitive detection of the making and breaking of chemical bonds. The system may be employed as a companion device to be used in the search for antibody and other novel catalysts. The cassette also has important clinical applications in the design of diagnostic reagents. In its fully encoded format this methodology is capable of both detecting and decoding chemical events.

1 Claim, 16 Drawing Sheets

|            | Primer 1 | Encoding sequence | Primer 2 |
|---|---|---|---|
| Template A | 5'- AGC TAC TTC CCA AGG | GAG CTG CTG CTA GTC | GGG CCC TAT TCT TAG- 3' |
| Template B | 5'- CTA AGA ATA GGG CCC | GAC TAG CAG CAG CTC | CCT TGG GAA GTA GCT- 3' |
| Template C | 5'- GGC GGC TTC CCA AGG | GAG CTG CTG CTA GTC | TAT TCT TAG GGG CCC- 3' |
| Template D | 5'- GGC GGC TTC CCA AGG | GAG CTG CTG CTA GTC | TAG GCG TAG GGG CCC- 3' |
| Template E | 5'- GGC GAC GTG ATG GGC | AAT TTG ATG ATA GAC | TAG GCG GAG GCG AGG- 3' |
| Template F | 5'- CGC AGG GTG AGT AAG | GCA GCA TAC GCA GCA | ATA GTG GAC GGA GCG- 3' |
| Template G | 5'- AGC TAC TTC CCA AGG | GAG CTC CTG CTA GTC | GGG CCC TAT TCT TAG - 3 |

Template A = SEQUENCE ID NO: 9
Template B = SEQUENCE ID NO: 10
Template C = SEQUENCE ID NO: 11
Template D = SEQUENCE ID NO: 12
Template E = SEQUENCE ID NO: 13
Template F = SEQUENCE ID NO: 14
Template G = SEQUENCE ID NO: 8

Figure 9

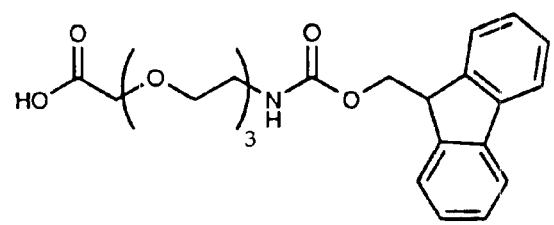
L-I
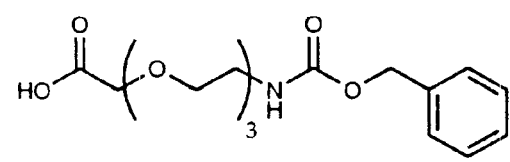
L-II
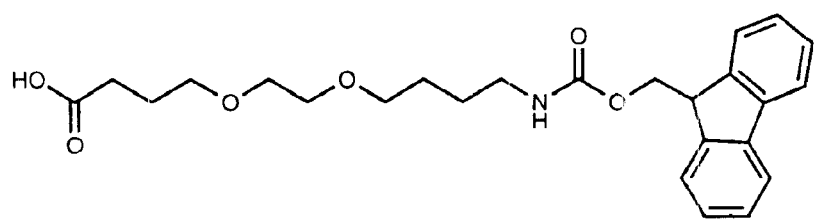
L-III
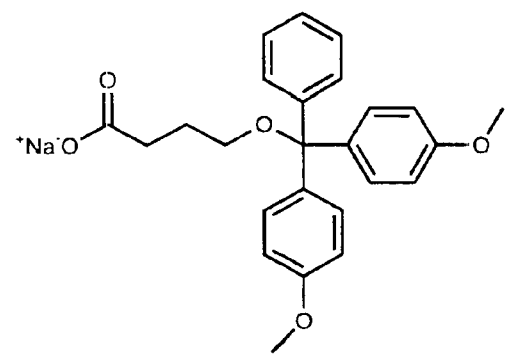
L-IV
Figure 15

US 6,849,398 B1

USE OF ENCODED REACTION CASSETTE

CROSS-REFERENCE TO RELATED APPLICATION

This is a US national phase application of international Application Ser. No. PCT/US96/00888, filed Jan. 18, 1996, which claims priority from and is a continuation-in-part application of U.S. patent application Ser. No. 08/374,050, filed Jan. 18, 1995, issued Sep. 24, 1996 as U.S. Pat. No. 5,559,000.

STATEMENT OF GOVERNMENT RIGHTS

This invention was made, in part, with government support under Grant No.'s GM 48351 from the National Institutes of Health. The U.S. government may have certain rights in the invention.

TECHNICAL FIELD

The invention relates to methods and reagents for assaying cleavage and ligation reactions and the activity of catalytic molecules which promote cleavage and ligation reactions. More particularly, the invention relates to assays which employ substrates covalently linked both to a solid phase matrix and to a nucleotide strand encoded to identify the substrate and including polymerization chain reaction (PCR) primer sequences for amplifying such encoded sequences.

BACKGROUND OF THE INVENTION

Cleavage and ligation reactions can be assayed by monitoring either the appearance of reaction products or the disappearance of substrates. For example, protein or peptide proteolysis can be monitored by following the appearance of cleavage products. Cleavage products may be separated from substrate by gel electrophoresis or by chromatographic separation and monitored by UV absorption or calorimetric assay. Similarly, polynucleotide ligation can be monitored by following the appearance of ligation products.

If the cleavage or ligation activity is low, the detection signal may require amplification to detect the reaction products. For example, radio labeled substrates may be synthesized and the resulting reaction products may be detected by radio immunoassay. Alternatively, if the substrate is conjugated to an enzyme which catalyzes a calorimetric reaction, the resultant reaction products may be detected by means of an enzyme immunoassay. Highly sensitive enzyme immunoassays have been developed. When employed at their limit of sensitivity, the signal produced by an enzyme immunoassay in response to the presence of reaction product becomes comparable to the background signal.

In the catalytic antibody field, antibody libraries are routinely screened in order to identify catalytically active antibody. There are two limitations to creating a useful catalytic antibody, viz.: 1.) designing a productive immunogen which is an analog of the substrate or reaction intermediate and producing an antibody library therewith; and 2.) screening the resultant antibody library for the desired catalytic activity. In short, the limitations are display and detection. The problem of display can be facilitated by converting the antibody diversity into a combinatorial library in phage where the recognition and replication functions are linked in a single entity and monitored by simple binding events. However, the screening of phage particles which display only a small number of catalytic antibody molecules requires a highly sensitive assay methodology. In such instances, the displayed catalytic activity may be only slightly higher than background activity. Prior art methods for assaying cleavage and ligation reactions sometimes lack the requisite sensitivity for identifying small quantities of low activity antibody. In some instances, catalytic antibody having a low level of catalytic activity can be useful if it is the only antibody identified to have such catalytic activity and/or if it is employed in an "evolutionary scheme" for generating antibodies having higher levels of catalytic activity. Accordingly, the sensitivity of the assay employed for screening an antibody library, may be the limiting factor with respect to the identification of useful antibody. The ease or difficulty of the assay may also limit the willingness of workers to perform these assays.

In instances in which one can obtain antibodies to the reaction product or substrate, an immuno-PCR assay may be constructed and employed as a detection system. (T. Sano et al., *Science* (1992): vol. 258, pages 120–122). An immuno-PCR assay is similar to an enzyme immunoassay except that the enzyme-antibody conjugate is replaced by an antibody conjugated to a PCR amplifiable polynucleotide strand. Immuno-PCR assays are highly sensitive. However, at very low levels of antigen, the immuno-PCR assay is limited by non-specific binding of the antibody-polynucleotide conjugate.

What is needed is a highly sensitive assay for detecting cleavage or ligation reactions. The assay should not employ an antibody conjugate and should have the lowest possible background signal. The assay should be labor efficient and should be adaptable for assaying any cleavage or ligation reaction.

SUMMARY OF THE INVENTION

The invention is directed to an encoded reaction cassette employable for detecting cleavage or ligation reactions and to assays employing such cassettes. Cassettes may be constructed for assaying any cleavage or ligation reaction. The cleavage or ligation reaction may be catalyzed or spontaneous, i.e., without benefit of a catalyitst.

A reaction cassette is designed for the highly sensitive detection of the making and breaking of chemical bonds. The system may be employed as a companion device to be used in the search for antibody and other novel catalysts. The cassette may also have important clinical applications in the design of diagnostic reagents. In its fully encoded format this methodology is capable of both detecting and decoding chemical events.

The assay of the present application was originally developed for application in the field of antibody catalysis. However, it may also be employed for assaying any synthetic or enzymatic reaction, including those important to diagnostic assays in medicine. When one is using the cassette to search for a single reaction, only one DNA sequence is necessary. However, in a fully encoded format, one can test multiple substrates simultaneously by using unique polynucleotide sequences for each substrate. The nature of the reaction that occurred may be simply determined by the sequence of the polynucleotide either after the PCR reaction or upon cloning of the polynucleotide according to the method of A. D. Mirzabekov (*TIBTECH* (1994): vol. 12, pages 27–32). In essence, one can create an encoded combinatorial library of substrates to learn about reaction specificities. One can design systems in which a combinatorial library of catalysts is screened against a combinatorial library of substrates to find new catalysts and refine their substrate specificity in a single operation. Finally, the disclosed method for constructing encoded cassettes may be adapted to an operating procedure in which a substrate cassette is built as a companion to any experiment where one is searching for a new catalyst. This enables the researcher or investigator to design experiments which are independent of whether the reaction products can be easily assayed by prior art methods. Thus, each time one contemplates searching for an enzyme the first step is to construct an encoded reaction cassette to detect reactivity.

More particularly, the invention is directed to an encoded reaction cassette for assaying a cleavage reaction. The reaction cassette includes a substrate covalently linked to a solid phase matrix, wherein the substrate is of a type which is suspectable to cleavage by means of the cleavage reaction. Linked to the substrate is a first polynucleotide which includes a first PCR primer sequence, an encoding sequence, and a second PCR primer sequence. The encoding sequence is positioned between the first and second PCR sequences. In a preferred embodiment, the encoded reaction cassette may also include a first and second linker. The first linker covalently links the solid phase matrix to the substrate. The second linker covalently links the substrate to the first polynucleotide. Peptides are preferred substrates. However, any cleavable substrate may be employed. In an alternative embodiment the encoded reaction cassette may include one or more additional polynucleotides linked to the substrate for further amplifying the signal. These additional polynucleotides also include the same first PCR primer sequence, encoding sequence, and second PCR primer sequence and may be linked to the substrate via additional linkers.

The invention is also directed to an admixture of cleavage products from an encoded reaction cassette which has been exposed to a cleavage agent. This admixture includes a solid phase cleavage product and a soluble phase cleavage product. The solid phase cleavage product includes a first cleavage product of a substrate covalently linked to the solid phase matrix. The soluble phase cleavage product includes a second cleavage product of the substrate covalently linked to the first polynucleotide. The invention is also directed to a method for detecting a cleavage agent within a sample. The method comprises the following steps. In the first step, the sample is admixed with an encoded reaction cassette under reaction conditions for promoting cleavage of the substrate to produce a cleavage products. If the sample has cleavage activity, cleavage products will be generated, i.e., a solid phase cleavage product and a soluble phase cleavage product. In the second step, soluble phase cleavage product is separated and isolated from the solid phase cleavage products and from uncleaved encoded reaction cassettes. In the third step, the encoding sequence of the polynucleotide of the soluble phase cleavage product isolated in the second step is amplified by means of a polymerization chain reaction (PCR). In the fourth step, the amplified encoding sequence amplified is detected. And, in an alternative fifth step, the signal obtained in the fourth step is correlated with known substrates and/or cleaving agents to obtain quantitative results.

Another aspect of the invention is directed to an admixture of unligated reactants for producing an encoded ligation cassette for assaying a ligation reaction. The admixture may include a solid phase ligation component and a soluble phase ligation component. The solid phase ligation component includes a first ligation reactant covalently linked to a solid phase matrix. The soluble phase ligation component includes a second ligation reactant covalently linked to a first polynucleotide. As before, the first polynucleotide includes an encoding sequence positioned between a first PCR primer sequence and a second PCR primer sequence. The first and second ligation reactants are capable of ligation in the presence of a ligating agent to join the solid phase and soluble phase ligation components so as to form an encoded ligation cassette. In a preferred embodiment, the first and second ligation reactants are fragments of a ligatible oligonucleotide. However, any pair of ligatible molecules may be employed. The encoded ligation cassette is analogous to the encoded reaction cassette except that a ligation product separates the solid phase matrix from the first polynucleotide. However, unlike the encoded reaction cassette, the encoded ligation cassette need not be susceptible to cleavage by a cleavage agent. Preferred ligating agents have ligation activity with respect to the first and second ligation reactants. More particularly, a preferred ligation agent is polynucleotide ligase and preferred first and second ligation reactants are ligatible oligonucleotides.

The invention is also directed to a method for detecting a nucleotide ligating agent within a oligonucleotide sample. The method includes several steps. In the first step, the sample is combined with an admixture of ligation components. The resultant admixture is the incubated for producing an encoded ligation cassette. In the second step, the encoded ligation cassette formed above is then separated and isolated together with unligated portions of the solid phase ligation component from the unligated portion of the soluble phase ligation component. The encoding sequence of the polynucleotide of the encoded ligation cassette may then be amplified by means of PCR, detected, and correlated with the presence of the ligation agent. Polynucleotide ligase is a preferred ligation agent. In this instance, the ligation product included within the encoded ligation cassette is a polynucleotide susceptible to ligation by the ligase.

The encoded reaction cassette operates through the liberation (bond cleavage event) or capture (bond formation event) of a polynucleotide that can be amplified and decoded. Chemical methods for the synthesis and assembly of this device are disclosed together with a detailed characterization and optimization of the parameters that influence its sensitivity and practicality. In the bond cleavage detection mode, using α-chymotrypsin as an exemplary catalyst, the specificity of the reaction cassette is demonstrated through the selective recognition and cleavage of peptide substrates differing in sequence by only one amino-acid ($Ala_2$-Tyr-$Ala_2$ versus $Ala_2$-Phe-$Ala_2$). The cassettes sensitivity (0.1–1 $\mu$moles, 5–50 nM) is the same whether using 0.01 mg (1 bead) or 10 mg (10000 beads), but is dependent on the concentration of α-chymotrypsin. The amount of this enzyme, however, can be decreased to as little as 2400 molecules provided the concentration is kept $\geq$5 nM. In the bond formation detection mode, α-chymotrypsin catalyzed peptide bond formation was not possible because of hindrance reasons, whereas chemically catalyzed bond formation (reductive amination of an aldehyde) could be performed, and was used as the prototype reaction for the demonstration of the second part of the principle of the reaction cassette, namely, the detection of the formation of a chemical bond.

BRIEF DESCRIPTION OF THE FIGURES

FIG. 9 illustrates the templates studied to improve the polymerase chain reaction (PCR) (SEQ ID NOS. 8–14).

FIG. 15 illustrates the chemical structure of spacer units (L-I to L-IV) used in the construction of the cassettes.

DETAILED DESCRIPTION

Design Features of the Cassette

The invention combines two prior art methods, viz.: 1. the technique of synthesizing polymers on solid support; and 2. the technique of PCR (Polymerase Chain Reaction). The overall approach is illustrated in FIG. 1.

Figure 1:
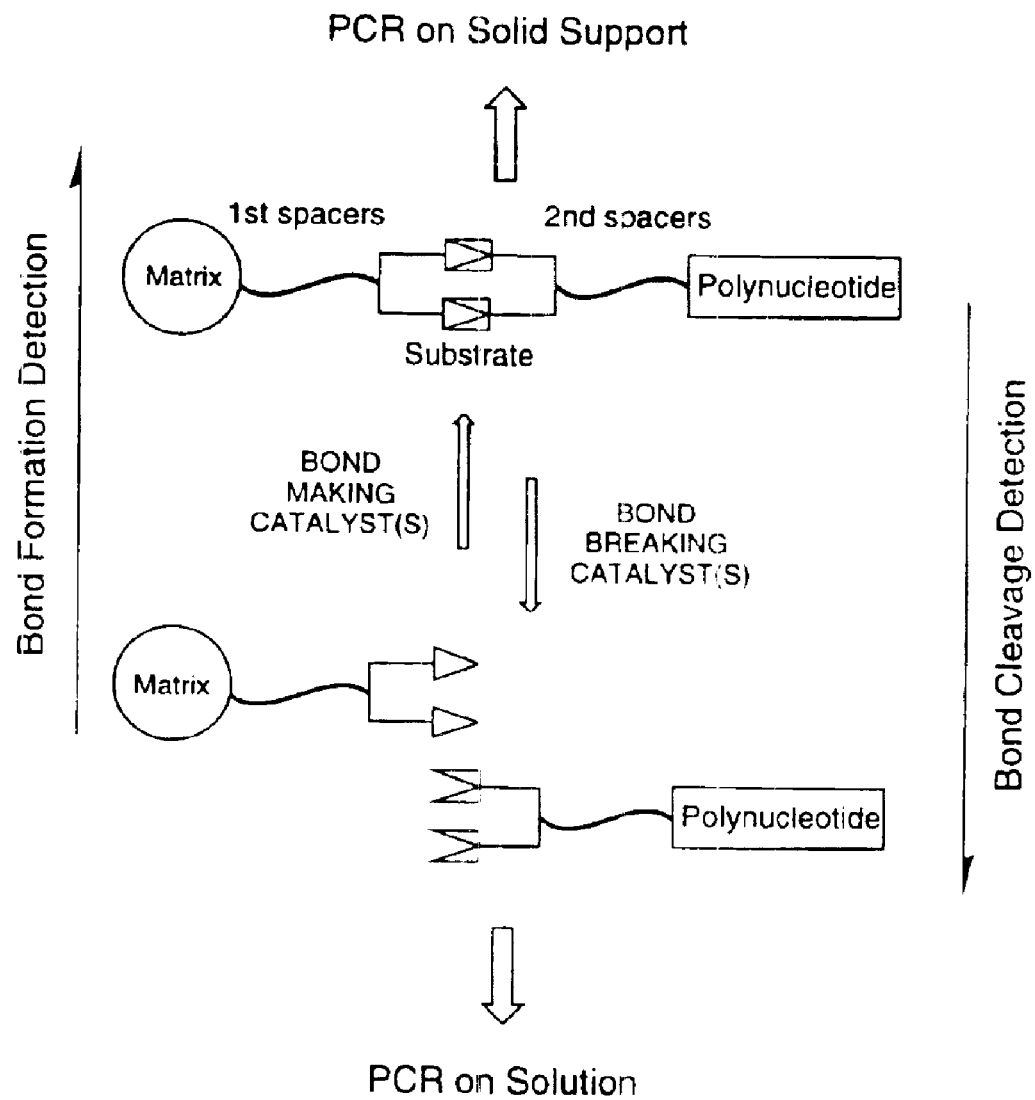
FIG. 1 illustrates the principle of the reaction cassette.

The central operative feature of the reaction cassette is the liberation (cleavage event) or capture (bond formation) of a polynucleotide containing two primers (FIG. 1). Thus, when an appropriately functionalized solid support (FIG. 1) is exposed to a catalyst or a library of catalysts that are able to selectively cleave the reaction cassette at the substrate juncture, single stranded DNA (polynucleotide) will be released and can be amplified by the PCR. Furthermore, the sequence of the polynucleotide may be chosen in such a way that it reflects the nature of the substrate, so that a library of encoded substrates can be designed. When substrate libraries such as these are exposed to a library of catalysts one can identify not only the catalyst but also the substrate since the sequence of the cleaved polynucleotide encodes and thus identifies which substrate sequence has been cleaved. In addition to the above methodology, our cassette reaction technique allows one to follow a bond formation event via the inverse pathway (FIG. 1). In this initial report we describe the application of our methodology to the study of enzyme catalyzed bond cleavage.

Three generations of reaction cassettes are disclosed herein. The first generation is based on Controlled Pore Glass (CPG) solid support. The second generation is based on a 70% w/w copolymer of polyethyleneglycol and polystyrene (TentaGel). The third generation is based on a composite matrix (NovaSyn KD).

Matrix Support:

The ideal support for a reaction cassette is mechanically and chemically compatible with the synthetic techniques used to assemble the cassette (peptide and DNA synthesis) while also being accessible to the catalyst employed (enzymes, abzymes, etc.). Polystyrene based matrices, for instance, are too hydrophobic for their use in enzyme catalyzed reactions while CPG was inappropriate due to poor chemical and mechanical stability (liberation of the polynucleotide-substrate conjugate leads to an undesired background reaction). TentaGel was found to be mechanically stable and chemically compatible with peptide substrates and DNA synthesis. However, this matrix is not preferred because it is to hydrophobic in character and does not allow optimal accessibility to the enzyme. For this reason, the third generation cassettes were designed and are disclosed herein. NovaSyn KD resin, a composite matrix derived from polydimethylacrylamide gel retained within a macroporous structure of kieselguhr inorganic particles was used. This matrix is more hydrophilic, mechanically and chemically stable and more compatible with biocatalysis. (Meldal, M.; Svendsen, I.; Breddam, K.; Auzanneau, F-I. *Proc. Natl. Acad. Sci. USA* 1994, 91, 3314.)

Spacers:

The spacers are preferably heterobifunctional, chemically stable, and compatible with both substrate and DNA synthesis. One end should be readily attachable to the substrate portion and the other should be equipped with a hydroxyl functionality for DNA synthesis.

The first spacer on the cassette is located between the matrix and the substrate, while the second between the substrate and the polynucleotide portion (FIG. 1). The length of both spacers is crucial for the success of the methodology. (Nielsen, J.; Janda, D. K.; Brenner, S. *J. Am. Chem. Soc.* 1993, 115, 9812.) For CPG and NovaSyn KD, a distance of at least 30–40 Å between the resin and the substrate is preferred in order to avoid hindrance that may result from proximity to the matrix core. This is a distance corresponding to twice the length of spacer II. TentaGel is already endowed with a long polyethyleneglycol chain which serves as the first spacer. The length of the second spacer (between the substrate and the polynucleotide) is disclosed to be less important for the catalytic reaction studied but was critical for DNA synthesis (vide infra).

Figure 2:
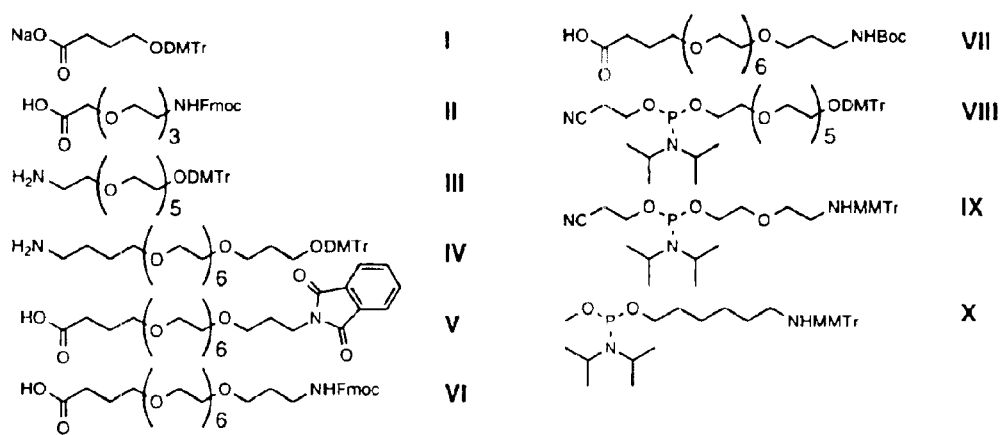
FIG. 2 illustrates the spacers which are used for the assembly of the reaction cassettes.

Different types and combinations of spacers for the construction of the cassettes are disclosed in FIG. 2. Spacers I–VII were synthesized while VIII and IX (Glen Research) and X (Millipore) are commercially available. Spacers I and II were prepared according to literature procedures and were introduced in our initial design (first and second generation cassettes). The synthesis of Spacer I is disclosed by Schaller et al. (Schaller, H.; Weimann, G Lerch, B.; Khorana, H. G. *J. Am. Chem. Soc.* 1963, 85, 3821.) The synthesis of spacer II is disclosed by Nielson et al. (Nielsen, J.; Janda, K. D. *Methods* 1994, 6, 361.) Spacer I is the shortest spacer. In many instances, it is too tight for optimal reactivity between catalyst and substrate. Its preferred use is in sequence with other spacers. Spacer XX was found to be chemically labile at the acetoxy bond under the strongly acidic and basic conditions required in SPPS (Boc-amino acid chemistry) and DNA synthesis respectively. (Stewart, J.; Young, J. *Solid Phase Peptide Synthesis*; Pierce Chemical Company: Rockford, Ill., 1984.)

Figure 3:
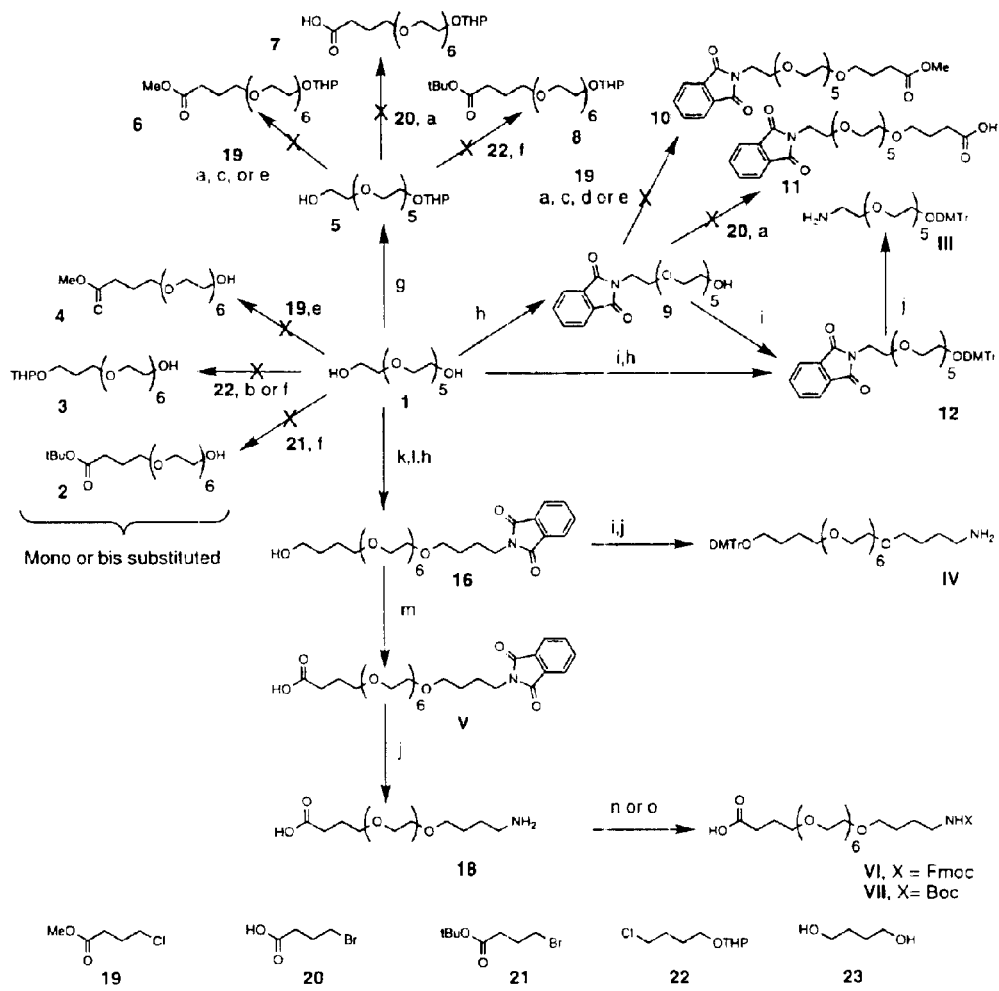
FIG. 3 illustrates the synthetic scheme for the preparation of spacers III–VII. The indicated synthetic steps are as follows: (a) K$_2$CO$_3$, DMF, 90–100° C.; (b) Cs$_2$CO$_3$, KI, DMF, 90–100° C.; (c) Cs$_2$CO$_3$, n-Bu$_4$NI, DMF, 85° C.; (d) Ag$_2$O, n-Bu$_4$NI or KI, THF, with or without sonication, 2° C.; (e) NaH, THF, 20° C.; (f) Na, THF, 20° C.; (g) DHP, MeOH, 1 drop HCl concd; (h) DEAD, PPh$_3$, Phtalamide, THF, 20° C.; (i) DMTrCl, pyridine, 20° C.; (j) (NH$_2$)$_2$, ethanol, 80° C.; (k) TsCl, pyridine, 20° C.; (l) Na, 23; (m) PDC, DMF, 20° C.; (n) FmocCl, Na$_2$CO$_3$, dioxane-H$_2$O, 0° C. to 20° C.; (o) (Boc)$_2$O, Et$_3$N, DMF, 0° C. to 20° C.

Spacers III and IV have free amino groups and can be attached to a substrate with a leaving group or carboxy terminus. Spacers V–VII are the longest; they can form an amide bond with peptide substrates and can be attached in sequence of two or more as opposed to spacers I, XII, and IV. Spacers V–VII were used in combination with spacers I, III or IV. Interconversion of these spacers allows for the synthesis of DNA at the terminal hydroxyl group generated. Spacer VIII can be automatically introduced between the substrate and the polynucleotide on a DNA synthesizer, this provided that I, XII or IV are already attached, or the substrate has a hydroxyl functionality. The deprotection step (hydrazine/ethanol (1/1)) required to quantitatively free the amino terminus of V was found to partially cleave the substrate from the resin. At lower hydrazine concentrations (0.2 M) the reaction is slow (24 hours) and incomplete (80–90%). (Bertozzy, C. R.; Bednarski, M. D. *J. Org. Chem.* 1991, 56, 4326.). This spacer is preferably employed with for more stable substrates. Spacers VIII–X were used to derivatize the oligonucleotide at the 3' end (DNA synthesizer ready) for studies on bond formation detection. The synthetic scheme for the preparation of III–VII is shown in FIG. 3.

Substrates:

α-Chymotrypsin is employed as an exemplary catalyst for the implementation of the reaction cassette. This enzyme is known to cleave amide bonds at the C-terminus of aromatic and hydrophobic amino acids such as Leucine, Methionine, Phenylalanine, Tyrosine. (Hess, G. P. in The Enzymes, Boyer P. D. (Ed.), Academic Press: New York, 1971, pp. 213–248.) This enzyme is also known to catalyze the formation of a peptide bond between Tyrosine methyl ester and the primary amine of Alanine. (Lane, J. W.; Hong, X.; Schwabacher, A. W. *J. Am. Chem. Soc.* 1993, 115, 2078.) Substrates 81–87 (FIG. 4) were assembled according to standard Boc and/or Fmoc methodologies. (Atherton, A.; Sheppard, R. C. *Solid Phase Peptide Synthesis: A Practical Approach*, oxford University Press: Oxford, 1989.)

Figure 5:
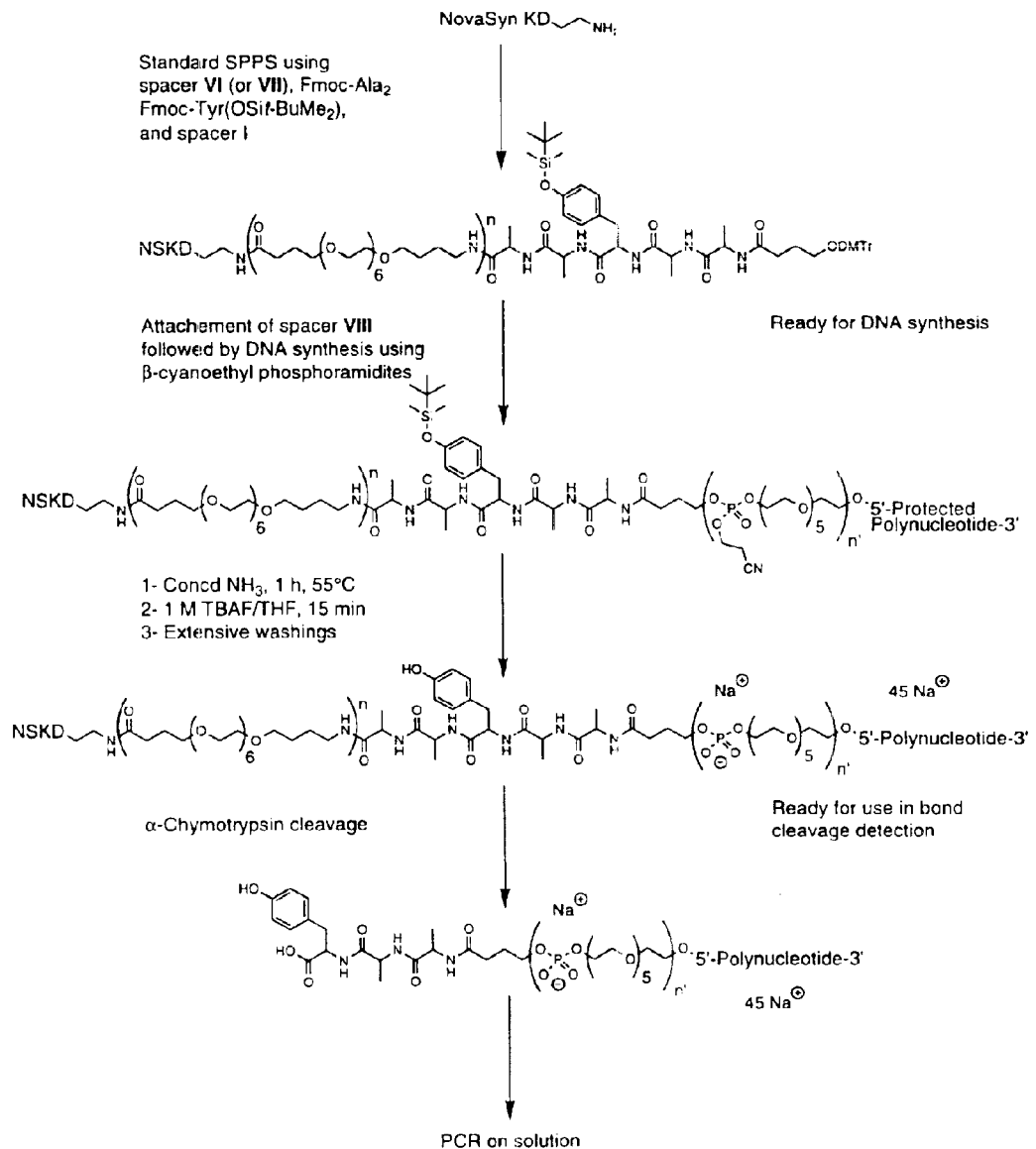
FIG. 5 illustrates the synthesis and use of the reaction cassette for the detection of α-chymotrypsin catalyzed bond cleavage. The top reaction shows the use of SPPS (solution phase peptide synthesis) on a NovaSynKD(CH$_2$CH$_2$NH$_2$) matrix with the spacer VI or VII, Fmoc-Ala$_{21}$ Fmoc-Tyr (OSit-BuMe$_2$), and spacer 1. The next reaction shows the attachment of spacer VIII which is followed by DNA synthesis using β-cyanoethyl phosphoramidites to afford a fully protected reaction cassette which is sequentially deprotected with concentrated ammonia and TBAF followed by extensive washings. The cassette is then ready for use in bond cleavage detection upon exposure to α-chymotrypsin followed by PCR amplication and assay (SEQ ID NO. 7).

The peptides 61 and 82 were used in the first generation, while S3–S7 were used in the second and third generation cassettes. α-Chymotrypsin cleaves substrate S4 ~10 fold more efficiently than S3, and ~$10^3$ fold more efficiently than S1, as estimated from data obtained for similar peptides, viz., Baumann, W. K.; Bizzozero, S. A.; Dutler, H. *Eur. J. Biochem.* 1973, 39, 381; and Fisher, G.; Bang, H.; Berger, B.; Schellenberger, A. *Biochimica Biophysica Acta* 1984, 791, 87. This characteristic may be employed to probe the specificity of α-chymotrypsin within our cassette system. Peptide S4 is one of the best substrates of α-chymotrypsin. Accordingly, this substrate is employed herein to exemplify a preferred lower limit of sensitivity of the cassette system. Peptide S7 was prepared in order to probe the interaction at the P4, P5, P4' and P5' sites of α-chymotrypsin. Peptide 88 was prepared in 5 steps (FIG. 7) using standard solution phase peptide chemistry (Supplementary Material) and was used in the detection of enzyme catalyzed bond formation. The synthetic procedure used to assemble the cassette is illustrated in FIG. 5 with NovaSyn KD as solid support using spacers I, VI (or VII) and VIII. This synthetic scheme is rapid and straightforward since Fmoc-Ala$_{217}$ and Fmoc-Tyr(OSit-BuMe$_2$) were used as building blocks in this synthesis. (Fisher, P. M. *Tetrahedron Lett.* 1992, 33, 7605.) The first and second spacers are attached according to standard SPPS. Spacer VIII is introduced automatically on the DNA synthesizer employing the same procedure used to assemble the polynucleotide. Indeed, this spacer can be attached in sequence in one or more copies. Upon completion of DNA synthesis, the polynucleotide is deprotected, followed by a 15 min incubation in 1 M TBAF in THF to remove the silicone protecting group of Tyrosine. After this step the cassette is ready for use in the bond cleavage detection mode.

Figure 6:
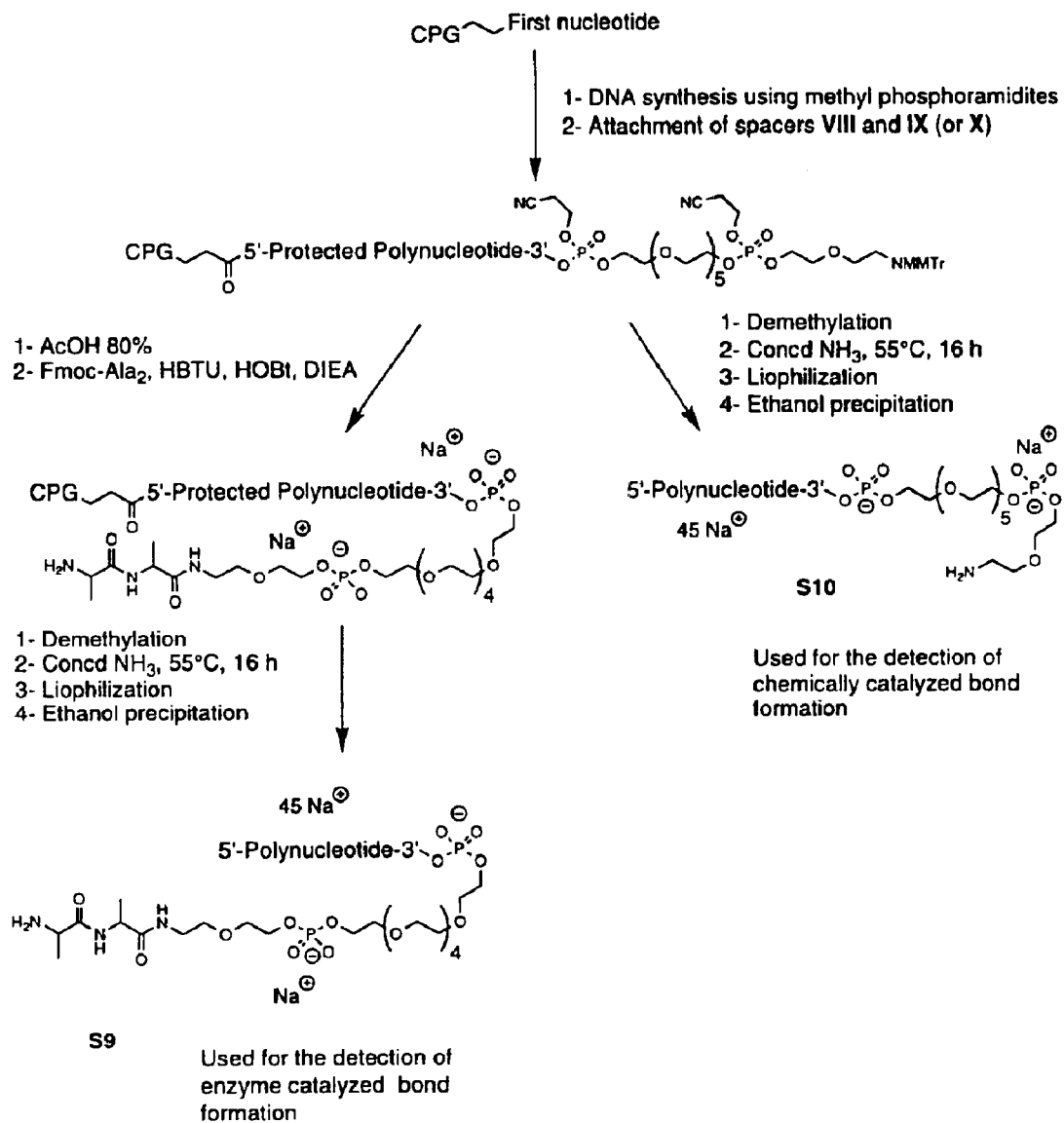
FIG. 6 illustrates the synthesis of the east side (S9, S10) of the reaction cassette for the detection of enzymatically and chemically catalyzed bond formation.

For bond formation the units of the substrate to be attached on the resin are prepared separately. FIG. 6 shows the synthesis of the east side of the reaction cassette: The polynucleotide-peptide conjugate (S9) and the polynucleotide amino-functionalized at the 5' end (S10). The S9 unit was prepared following conventional DNA synthetic procedures using methyl phosphoramidite monomers that are stable to the conditions of SPPS. The unit S10 could be prepared in a similar manner (same monomers) or using Expedite β-cyanoethyl phosphoramidites monomers (Millipore) which are more easily deprotected.

DNA Synthetic Procedures:

Standard DNA synthesis was improved upon using CPG or polystyrene solid supports. CPG does has less preferred chemical and mechanical properties (vide supra). Polystyrene based matrices have less preferred hydrophobic characteristics.

The standard 1 µmole procedure of the 394 Applied Biosystem DNA synthesizer (termed procedure A) using phosphoramidites chemistry was modified for the second generation cassettes (termed procedure B) as described previously. (Gait, M. J. *Oligonucleotide Synthesis: A practical Approach*: Oxford University Press: New York, 1990.) Procedure B was further modified (termed procedure C) in order to adapt it to CPG, NovaSyn KD and TentaGel resins (see experimental section). Table 1 shows the improvements in average stepwise yield (ASWY) and overall yield (OAY) using procedures A–C on CPG (cassette C1), TentaGel (cassette C10) and NovaSyn KD (cassette C29).

TABLE 1

ASWY (average stepwise yield) and OAY (overall yield) for DNA synthesis using different resins and modified procedures.

|  | Procedure A[a] | Procedure B[b] | Procdure C[c] |
|---|---|---|---|
| CPG (C1) | 98.8%, 58.1% | 99.3%, 72.9% | 99.4%, 76.3% |
| TentaGel (C10) | Fails[d] | 96.9%, 24.2% | 99.2%, 69.7% |
| NovaSyn KD (C29) | Fails[d] | 95.0%, 9.9% | 98.5%, 42.4% |

[a]1 micromole standard procedure of the 394 Applied Biosystem DNA Synthesizer.
[b]Same as procedure A but modified as in reference 5.
[c]Same as procedure A, but modified as in the methods section.
[d]An ASWY < 95% is considered a failure because the OAY in this case is < 9.9%.

Two other factors played a major role in the success of the DNA synthesis, the first being the length of the spacer between the substrate and polynucleotide and the second being the loading of the resin. In general, longer spacers between the substrate and the polynucleotide and lower loadings result in better ASWY's for DNA synthesis (see Tables 2–4). For instance, on TentaGel with procedure B, the ASWY is 96.9% with I (C10), 98.8% with VI (or VII) and I (C20), and 99.8% with 2(VI) and I (C21). On the same resin with I, and procedure B, when the loading is 172.1 µmoles/g (C12) DNA synthesis fails, and when the loading is 59.9 µmoles/g (C10), DNA synthesis works successfully with an ASWY of 96.9%. With high loading, the synthesis fails, regardless of the presence or absence of a long spacer between the substrate and the polynucleotide.

In all cases studied, the yield of DNA synthesis after deprotection with concentrated ammonia varies from 24% to 100% depending on the cassette (~70% on average, see last column of Tables 3 and 4). Without the substrate portion, the deprotection is quantitative. Taken together with the fact that concentrated ammonia affects the matrix to a lesser extent before DNA synthesis (10–20% loss), these results indicate that during DNA synthesis, labile bonds, branching points, etc., are generated which upon treatment with conc. ammonia are eliminated. The amplitude of this side reaction may sometimes vary from one cassette to another.

TABLE 2

Reaction cassettes prepared with CPG solid support and template A as the tag.

| N° | 1st Spacer | Substrate | 2nd Spacer | Loading before DNA synthesis[a,f] | DNA synthesis ASWY, OAY[b,f] | Loading after DNA synthesis[c,f] | OAY before DNA deprotection[d] | Loading after DNA deprotection[e,f] |
|---|---|---|---|---|---|---|---|---|
| C1 | 2II | S1 | I | 43.7 | 98.8%, 58.1% | 18.8 | 43% | 0% |
| C2 | " | S2 | " | 43.2 | 98.8%, 58.1% | 17.4 | 40.3% | " |
| C3 | " | S1 | II-I | 32.2 | 99.3%, 72.9% | 23.5 | 72.9% | " |
| C4 | " | S2 | " | 31.3 | 99.4%, 76.3% | 24 | 76.7% | " |
| C5 | " | S1 | 2II-I | 24.6 | 98.9%. 60.8% | 12.1 | 49.2% | " |
| C6 | " | S2 | " | 27.9 | 99.4%. 76.3% | 21.5 | 77.2% | " |

[a]Micromoles of peptide substrate per gram of resin;
[b]Average stepwise yield (ASWY) and overal yield (OAY) using procedure A, B or C (see methods section);
[c]Micromoles of peptide-polynucleotide hybrid per gram of resin before DNA deprotection;
[d]OAY of DNA synthesis determined from the ratio of loading before (column 5) and after (column 7) DNA synthesis;
[e]Micromoles of peptide-polynucleotide conjugate per gram of resin after DNA deprotection with concentrated ammonia;
[f]Data determined using the dimetoxytrityl cation assay and/or the Fmoc assay.

TABLE 3

Reaction cassettes prepared with TentaGel solid support and template A as the tag.

| N° | 1st Spacer | Substrate | 2nd Spacer | Loading before DNA synthesis[a,f] | DNA synthesis ASWY, OAY[b,f] | Loading after DNA synthesis[c] | Loading after DNA deprotection[d,f] | OAY after DNA deprotection[e,f] |
|---|---|---|---|---|---|---|---|---|
| C7 | $(CH_2CH_2O)_{-68}$ | S3 | I | 50.8 | 98.4%, 48.4% | 24.6 | 21.5 | 87.4% |
| C8 | " | S4 | " | 44.3 | 98.5%, 50.7% | 22.5 | 17.2 | 76.6% |
| C9 | " | " | " | 50.8 | 98.1%, 42.2% | 21.4 | 16.7 | 77.9% |
| C10 | " | " | " | 59.9 | 96.9%, 24.2% | 14.5 | 7 | 48.3% |
| C11 | " | " | " | 140.7 | Fails[g] | — | — | — |
| C12 | " | " | " | 172.1 | Fails[g] | — | — | — |
| C13 | " | S5 | " | 64.5 | 98.0%, 40.3% | 26 | 9.6 | 36.9% |
| C14 | " | " | " | 87.8 | Fails[g] | — | — | — |
| C15 | " | S6 | III | 42.5 | 97.9%, 38.5% | 16.4 | 14 | 85.6% |
| C16 | " | " | III-VIII | " | 99.3%, 72.9% | 31 | 12.4 | 40.0% |

TABLE 3-continued

Reaction cassettes prepared with TentaGel solid support and template A as the tag.

| N° | 1st Spacer | Substrate | 2nd Spacer | Loading before DNA synthesis[a,f] | DNA synthesis ASWY, OAY[b,f] | Loading after DNA synthesis[c] | Loading after DNA deprotection[d,f] | OAY after DNA deprotection[e,f] |
|---|---|---|---|---|---|---|---|---|
| C17 | " | " | III-VIII | 92 | Fails[g] | — | — | — |
| C18 | " | " | IV | 38.2 | 97.8%, 36.8% | 14.1 | 14.4 | 100% |
| C19 | " | " | " | 88.2 | Fails[g] | — | — | — |
| C20 | " | S4 | VI-I | 52.6 | 98.8%, 58.1% | 30.6 | 15.9 | 52.0% |
| C21 | " | " | 2VI-I | 23.1 | 99.8%, 91.4% | 21.1 | 9.7 | 45.9% |
| C22 | " | " | 2VIII- | " | 98.5%, 49.9% | 11.5 | 7.2 | 62.5% |
| C23 | " | " | 2VI-I-3VIII | " | 98.1%, 39.8% | 9.2 | 6.2 | 67.5% |
| C24 | " | " | 2VI-I-5VIII | " | 98.0%, 35.7% | 8.3 | 6 | 72.8% |
| C25 | " | S7 | I | 70.7 | [h] | — | — | — |

[a]Micromoles of peptide substrate per gram of resin.
[b]Average stepwise yield (ASWY) and overal yield (OAY) using procedure B or C (see methods section).
[c]Micromoles of peptide-polynucleotide conjugate per gram of resin determined using the loading before DNA synthesis (column 5) and the OAY of DNA synthesis (column 6).
[d]Micromoles of peptide-polynucleotide conjugate per gram of resin after DNA deprotection with concentrated ammonia.
[e]OAY determined from the ratio of loading before DNA synthesis (column 5) and after DNA synthesis and deprotection (column 8).
[f]Data determined using the dimetoxytrityl cation assay and/or the Fmoc assay.
[h]DNA synthesis was not performed on this resin, see text.
[g]An ASWY < 95% is considered as a failure because the OAY would be < 9.9%.

TABLE 4

Reaction cassettes prepared with NovaSyn KD solid support and with E as the tag.

| N° | 1st Spacer | Substrate | 2nd Spacer | Loading before DNA synthesis[a,f] | DNA synthesis ASWY, OAY[b,f] | Loading after DNA synthesis[c] | Loading after DNA deprotection[d,f] | OAY after DNA deprotection[e,f] |
|---|---|---|---|---|---|---|---|---|
| C26 | VI | S4 | I | 83.6 | 98.5%, 50.7% | 42.4 | 16.9 | 39.9% |
| C27 | " | " | I-VIII | " | 98.5%, 49.9% | 41.7 | 26.5 | 63.5% |
| C28 | " | " | I-2VIII | " | 97.0%, 23.9% | 20 | 17.7 | 88.6% |
| C29 | 2VI | " | I | 78.3 | 98.0%, 40.3% | 31.6 | 16.6 | 52.6% |
| C30 | " | " | I-VIII | " | 98.2%, 43.4% | 34 | 30.1 | 88.7% |
| C31 | " | " | I-2VIII | " | 97.9%, 36.9% | 28.9 | 24 | 83.1% |
| C32 | " | S7 | " | 62.2 | 97.5%. 30.4% | 18.9 | 9.3 | 49.1% |
| C33 | " | S7 | I | 62.2 | [g] | — | — | — |

[a]Micromoles of peptide substrate per gram of resin.
[b]Average stepwise yield (ASWY) and overal yield (OAY) using procedure C (see methods section).
[c]Micromoles of peptide-polynucleotide conjugate per gram of resin determined using the loading before DNA synthesis (column 5) and the OAY of DNA synthesis (column 6).
[d]Micromoles of peptide-polynucleotide conjugate per gram of resin after DNA deprotection with concentrated ammonia.
[e]OAY determined from the ratio of loading before DNA synthesis (column 5) and after DNA synthesis and deprotection (column 8).
[f]Data determined using the dimetoxytrityl cation assay and/or the Fmoc assay.
[g]DNA synthesis was not performed on this resin.

A preferred synthetic strategy utilized to build the east side of the reaction cassette for the detection of enzyme catalyzed bond formation is shown in FIG. 6. This unit (S9) requires the use of more stable monomers for DNA synthesis. A coupling step with Fmoc-Ala$_2$ has to be performed in the presence of a strong base (DIEA). Under such conditions, the usual β-cyanoethyl protecting group (used in bond cleavage detection) can be lost and thus lead to undesired side reactions. The methyl phosphoramidite monomers proved to be more appropriate as a result of their inherent stability. For chemically catalyzed bond formation this limitation does not apply, and methyl or β-cyanoethyl phosphoramidite monomers can be used to prepare 810 (FIG. 6).

PCR Protocols:

Two critical aspects of the encoded reaction cassette are the sequence and length of the tag. In terms of the tag length, it should be as short as possible for a better OAY in DNA synthesis. In addition, it must be specifically amplified with a high sensitivity.

Several templates (A–F, FIG. 9) were characterized under various PCR conditions, e.g., pH, [MgCl$_2$], (primer), [enzyme], cycles, and temperature. Templates A–F differ by the sequence of the primers and G/C content. These two factors are responsible for template tertiary structure and mispriming. Upon analyzing tertiary structure and self-complementary sequences within the template and with the primers using computer modeling (DNASIS, Amplify and OLIGO), it was determined that the primer sequence is the essential ingredient for efficient amplification. The reason for this is that the templates engaged are so short that they can be amplified at low temperature where mispriming occurs readily. With template A (1st and 2nd generation), templates B–E, and template F (third generation), the sensitivity could not be improved below $10^{-14}$ moles of template under PCR conditions previously reported without increasing non-specific amplification products.

In a preferred mode, Hot Start PCR techniques for the third generation cassettes, such as TaqStart PCR (Clontech), AmpliWax (Perkin-Elmer), and HotWax (Invitrogen). (Mullis, K. PCR Methods and App. 1991, 1, 1–4; and D'Aquilla, R.; Bechtel, L. J.; Videler, J. A.; Eron, J. J.; Gorczyca, P.; Kaplan, J. C. Nucl. Acids. Res. 1991, 13, 3749.) The latter technique is preferred and yield good best results. The technique is based on a wax containing $Mg^{++}$ which is added to the reaction mixture before cycling. Heating at 94° C. for 30 seconds before the first cycle liberates $Mg^{++}$ in solution and allows Taq polymerase to proceed. In this manner mispriming that can occur at low temperature cannot be amplified since $Mg^{++}$ is liberated only at high temperature. Because of its low density the melted wax remains on the surface of the aqueous layer which also serves to prevent evaporation of the solution. With Template E the sensitivity could be improved to $10^{-17}$ moles but the yield and specificity are poor (weak bands and non-specific products co-migrating with the desired product). Template F gave the best results under Hot Start PCR conditions using HotWax and modified PCR protocol (see experimental section). Now we were able to detect as little as 60–600 molecules of template on agarose gel with ethydium bromide staining. Finally it should be mentioned that it is preferred to work under strictly sterile conditions to avoid contamination and carry-over when such a small amount of molecules is to be detected. (Rolfs, A.; Schuller, I.; Finckh, U.; Weber-Rolfs, I. PCR: Clinical Diagnostics and Research; Springer-Verlag: Berlin Heidelberg, 0.1992, chapter 5; and Innis, M. A.; Gelfand, D. H.; Sninsky, J. J.; White, T. J.; (Eds) PCR Protocols. A Guide to Methods and Applications; Academic Press: San Diego, 1990.)

Figure 10:
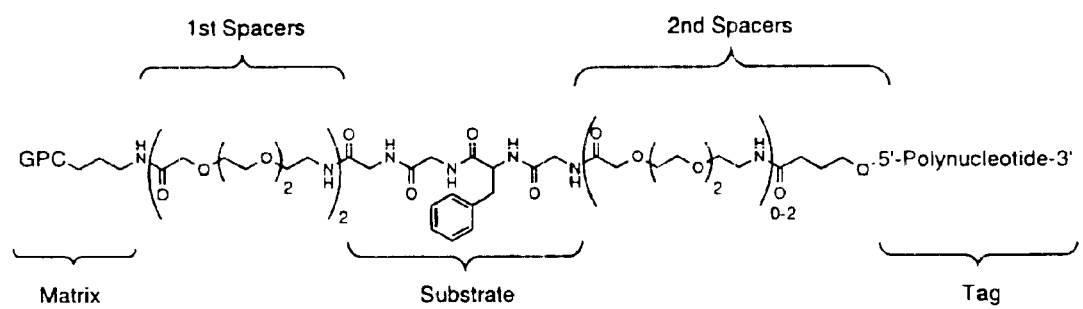
FIG. 10 illustrates the general scheme of the first generation reaction cassettes (C1–C6).

Bond Cleavage:

First Generation Cassette. This generation was assembled on CPG with (D) and (L) amino acids, and with different combinations of spacers using standard solid phase peptide and DNA synthesis. The ASWY for peptide synthesis was 95–98%, and ~99% for DNA synthesis (see Table 2 and FIG. 10). Template A (FIG. 9) and a combination of spacers I and II were used in this first generation.

Conventional ammonia deprotection of the polynucleotide leads to quantitative cleavage of the peptide-polynucleotide conjugate from the resin. This result was the same when Expedite phosphoramidites (Millipore) is employed. The method requires only a short exposure to concentrated ammonia, e.g., 1 hour instead of 16 hours. The cassette is not cleaved by the enzyme when the DNA is not deprotected. This result was attributed to its hydrophobic character when protected. Mild deprotection of the polynucleotide on the phosphate backbone (overnight incubation with DBU 0.5 M in anhydrous DMF) does not affect the reaction cassette. This partial deprotection makes the cassette more hydrophilic and allows α-chymotrypsin to reach and cleave the peptide substrate of the cassette leading to the liberation of the polynucleotide in solution. Unfortunately the background reaction (spontaneous cleavage) accounts for 25% of the reaction, and makes this first generation cassette impractical.

Second Generation Cassette.

Figure 11:
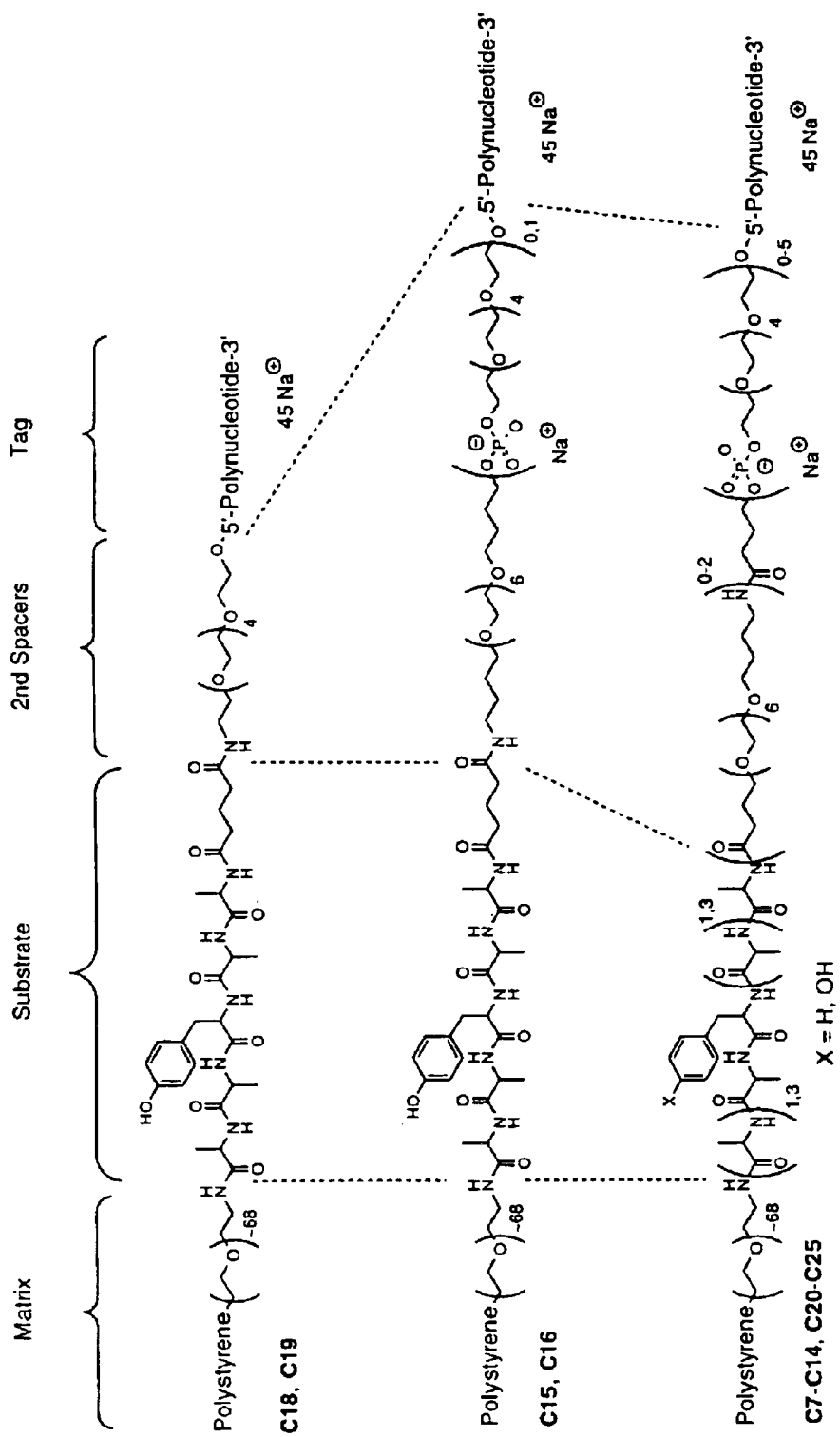
FIG. 11 illustrates the general scheme of the second generation reaction cassettes (C7–C25).
Figure 12:
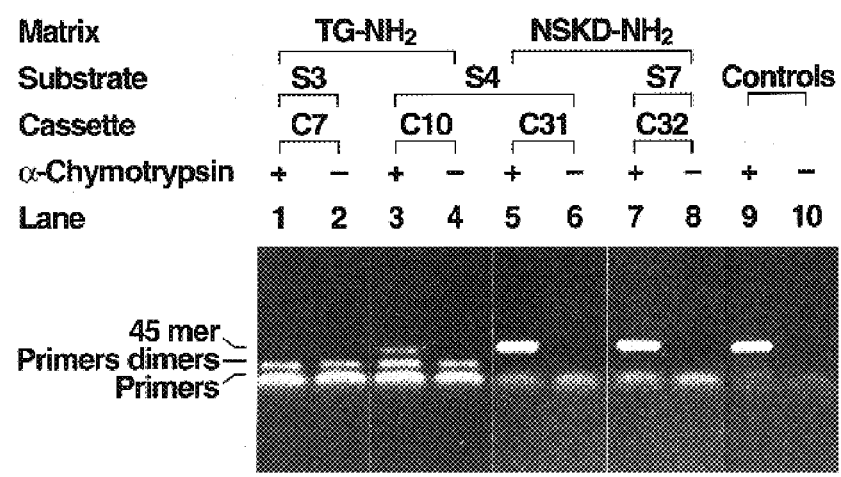
FIG. 12 illustrates bond cleavage detection. PCR products of samples from the medium containing the reaction cassette indicated on top of each lane, with or without α-chymotrypsin: Lanes 1, 3, 5, and 7 correspond to the PCR products of a sample from the medium containing α-chymotrypsin (5 nM), and Cassette C7, C10, C31, and C32 respectively; Lanes 2, 4, 6, and 8 correspond respectively to the same experiments without α-chymotrypsin. The positive control (Lane 9) corresponds to the PCR product of an authentic sample of the DNA 45mer. The negative control (Lane 10) corresponds to the same experiment without the DNA 45mer. TG-NH$_2$ and NSKD-NH$_2$ correspond respectively to unfunctionalized TentaGel and NovaSyn KD resins bearing an amino terminus group.
Figure 13:
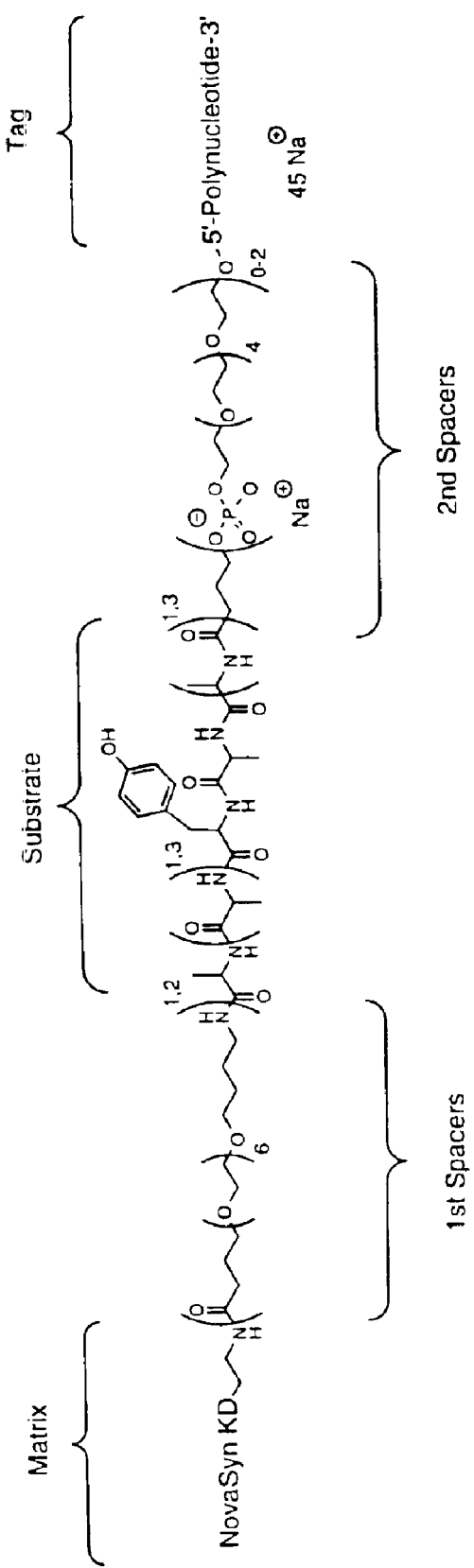
FIG. 13 illustrates the general scheme of the third generation reaction cassettes (C26–C32).

This generation is based on TentaGel resin. Several cassettes are disclosed herein, with both (L) and (D) amino acids, with different combinations of spacers and different loadings (FIG. 11 and Table 3). As opposed to CPG and NovaSyn KD based cassettes, TentaGel is already endowed with a long polyethyleneglycol side arm. It is not necessary to introduce a spacer between the resin and the substrate. All TentaGel based resins with a loading $\geq 80$ μmoles/g were eliminated from our studies because the cassette could not be assembled in good yields (Table 3).

α-Chymotrypsin cleavage of the substrate: a) in the presence and, b) in the absence of spermine (1 mM), c) with or, d) without DMSO (20%), e) with or, f) without BSA (1%), g) with or, h) without single stranded DNA binding protein (3.2 μM final concentration, Promega), I) with different concentrations of reaction cassette, j) with different enzyme concentrations and, k) over various incubation periods, are disclosed herein. Spermine and single stranded DNA binding protein were expected to minimize the interaction of α-chymotrypsin (overall charge +5 to +6) with the polynucleotide (overall charge –45). (Blow, D. W. in The Enzymes; Boyer P. D. (Ed.), Academic Press: New York, 1971, pp. 185–212.) Spermine did not affect the sensitivity of the reaction, while single stranded DNA binding protein inhibited the reaction. This latter finding may be due to hindered access to the substrate site upon binding to the polynucleotide. The concentration of reaction cassette as well as the incubation time did not improve the sensitivity, it only increased the background reaction. DMSO and BSA which were expected to minimize non-specific interactions with the matrix, also did not affect the sensitivity. As expected, (D) amino acid based cassettes were not cleaved. The length of the second spacer did not affect the sensitivity of the reaction cassette which in all cases studied did not exceed the previously reported, 0.1–1 μmoles (5–50 nM) α-chymotrypsin. If charge interactions are important, then the positively charged α-chymotrypsin may be sequestered in close proximity to the negatively charged substrate-polynucleotide conjugate, thus increasing its local concentration. This then could compensate for hindrance effects. With this generation cassette, C10 is cleaved under conditions were C. is not (Figure, lanes 1–4). Apparently, the reaction cassette discriminates between two very similar substrates differing with only one amino acid ((L)Ala$_2$-(L)Tyr-(L)Ala$_2$ versus (L)Ala$_2$-(L)He-(L)Ala$_2$). The difference in reactivity of α-chymotrypsin towards these two substrates in solution is estimated to be ~10 (see above). This result is relevant to the construction of encoded reaction cassettes libraries.

The fact that the sensitivity of the reaction cassette system stops at 0.1–1 μmole of α-chymotrypsin means that the uncatalyzed reaction is almost as fast as the reaction with 0.1–1 μmoles α-chymotrypsin. At first approximation, there is no apparent reason for the sensitivity to reach a minimum at this level. There are several possible answers for this question: a) $K_m$ can be affected by the microenvironment created by the resin or the conformation of the substrate which may decrease the affinity of the enzyme for the substrate, b) the uncatalyzed reaction is abnormally fast within this cassette system, c) the substrate is not fully _accessible to the enzyme (i.e. matrix is too hydrophobic or substrate hindered by DNA), d) PCR conditions are not optimal.

For the reaction to occur, the substrate has to be recognized by the catalyst; $K_m$ will thus directly affect the sensitivity of the reaction cassette. Assuming that the $K_m$ ($10^{-5}$ M at the best)[16] is 100 times higher for the substrate on the solid support ($K_{mapp}=10^{-3}$ M), the fraction of complex formed under the most favorable concentration conditions used ($125 \cdot 10^{-3}$ M of reaction cassette, $55 \cdot 10^{-9}$ M α-chymotrypsin) would be 0.92 ($4.625 \cdot 10^{-9}$ M). Assuming that $k_{cat}$ (100 s$^{-1}$ at the best) is not affected by the microenvironment and that all complexes formed are productive, the velocity of the enzyme would be 4.625 10$^{-7}$ Ms$^{-1}$ (4.625 10$^{-9}$ M 5 100 s$^{-1}$). Under the same concentration conditions, the velocity of the background reaction (peptide solvolysis) may be approximated to 3.65 10$^{-11}$ Ms$^{-1}$ (35 10$^{-9}$ s$^{-1}$ 5 125 10$^{-3}$ M). (Kahn, D.; Still, W. C. *J. Am. Chem. Soc.* 1988, 110, 7529.) The ratio of the velocities with and without enzyme is >10$^4$. According to this rough estimate, these encoded reaction cassettes should be able to detect at least 10$^{-17}$ moles of α-chymotrypsin (0.15 10$^{-12}$ moles 5 10$^{-4}$). Therefore, the sensitivity should not be limited by $K_m$. The second possibility may be ruled out as it would assume that the rate constant for an inactivated peptide bond solvolysis would be 3.85 10$^{-5}$ s$^{-1}$ (4.625 10$^{-7}$ Ms$^{-1}$/125 10$^{-3}$ M) which cannot be accounted for by a mere microenvironment effect. The third possibility concerning the accessibility of the substrate to the enzyme was examined using C25 (Table 3) and C33 (Table 4). These cassettes are lacking the polynucleotide portion and were used to probe the hindrance that may result from this unit. These cassettes were also chosen in order to investigate the enzyme's accessibility to the substrate in the second generation reaction cassettes since C33 is based on NovaSyn KD resin which has been shown to be compatible with biocatalysts. When these cassettes were incubated with α-chymotrypsin, C33 is quantitatively cleaved at the substrate portion leading to the liberation of HO-(L)Tyr-(L)Ala$_4$-I-OH in solution ($\lambda_{max}$=276 nm, ε=1450 M$^{-1}$cm$^{-1}$ in 0.1 M HCl), whereas C25 did not give rise to any UV detectable material in solution, indicating that, indeed, the enzyme does not have full access to the substrate on TentaGel resin, probably because of its hydrophobic character. The fact that we do see cleavage on agarose gel with TentaGel based cassettes is simply due to the powerful amplifying effect of the PCR. The fourth possibility was examined using decreasing concentrations of template A (FIG. 9) used in this study. The sensitivity leveled out at 10$^{-14}$ moles of template.

Third Generation Cassette.

The third generation cassette incorporates several improvements, viz.:
a) The PCR conditions and primer sequences are improved in order to increase sensitivity, by the design and use of template F,
b) The matrix material is selected to be compatible with the catalyst employed so as to further improve the sensitivity. A hydrophilic matrix such as NovaSyn KD is a preferred material.

The synthetic procedure using standard SPPS and phosphoramidite chemistries for the assembly of the third generation cassette is shown in FIG. 5. Template F containing 2 primers and an encoding sequence for Ala$_2$-Tyr-Ala$_2$ served as the tag for this generation.

Incubation of C26–C32 in the presence of α-chymotrypsin leads to the cleavage of the substrate portion and liberation of the polynucleotide which can be amplified and visualized on agarose Gel (Figure, for C31 for instance see lanes 5 and 6). C31 and C32 are cleaved with the same efficiency, indicating that our cassette system does not discriminate between substrate differing at the P3, P4, P3', and P4' positions. This then sets a limit to the specificity of this generation cassette (Figure, lanes 7 and 8). This information is crucial for the design of combinatorial encoded reaction cassettes. Unexpectedly, again the lower limit of sensitivity did not exceed 0.1–1 μmoles of α-chymotrypsin obtained with TentaGel although all parameters (incubation time, PCR sensitivity, choice of the resin, length of the spacers, DNA synthesis, etc.) were optimized for this study. Even more unanticipated were our findings with C30 that: a) the detection limit is the same whether we used ~0.01 mg (1 bead) or ~10 mg of reaction cassette. Although difficult to explain at this stage, the fact that 1 bead leads to the same sensitivity as 10000 beads will be extremely helpful and economical in the screening of combinatorial libraries of substrates and catalysts; b) after the completion of the reaction, 1 μl of the reaction media with the cassette and α-chymotrypsin can be diluted up to 10$^9$ fold and still give rise after the PCR to a band on agarose gel corresponding to the polynucleotide tag. In contrast 1 μl from the uncatalyzed reaction media no longer give rise to any detectable material after a 10$^3$ fold dilution. This experiment clearly delineates that 0.1–1 μmoles of the enzyme produces ~10$^6$ times more polynucleotide in solution than the background reaction and yet, it is the lower concentration of α-chymotrypsin that can be detected over the background. Although mathematically it should be possible to detect enzyme amounts ≧45 10$^{-21}$ moles (0.15 10$^{-12}$ moles 5 1/10$^6$ 5 1/25=2400 molecules), experimentally, this amount cannot be detected unless α-chymotrypsin remains at a concentration ≧5 nM. (0.15 10$^{-12}$ moles corresponds to the lowest detectable amount of α-chymotrypsin; 1/10$^6$ corresponds to the dilution factor of the reaction media that still can give rise to a signal over background on agarose gel; 1/25 comes from the fact that only 1 μl of the reaction media (25 μl) was used for amplification by the PCR.) Possibly the enzyme interacts strongly with the polynucleotide and cannot reach the substrate until all sites are saturated.

Bond Formation Detection:.

Figure 7:
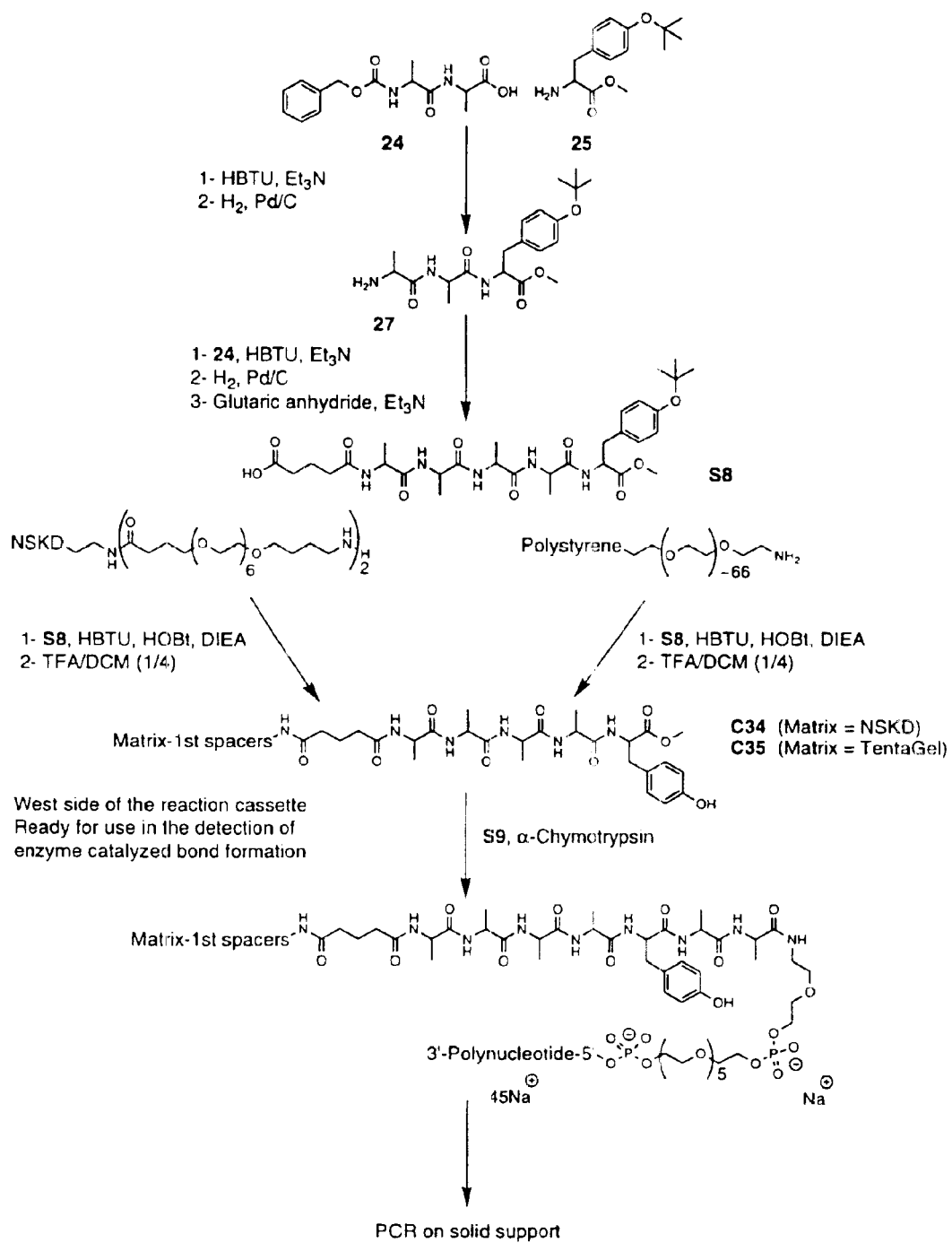
FIG. 7 illustrates the synthetic approach for the detection of enzyme catalyzed bond formation: Coupling of the west side (C34 or C35—derived from commercially available compounds 24 or 25) to the east side (S9—synthesis shown in FIG. 6). The cassette is then ready for use in an enzyme catalyzed bond formation upon exposure to α-chymotrypsin followed by PCR amplication on a solid support and detection by fluorescent assay.
Figure 14:
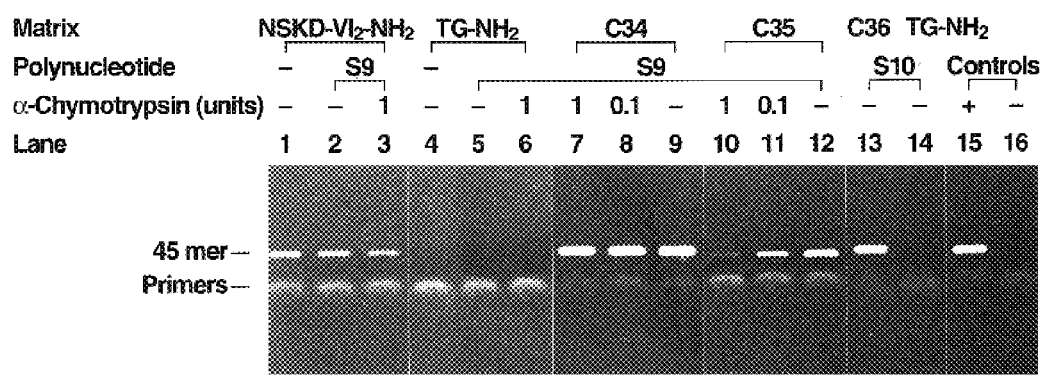
FIG. 14 illustrates bond formation detection. PCR products of one bead from the medium containing the functionalized or unfunctionalized resin (NSKD-VI$_2$-NH$_2$, TG-NH$_2$, C34, C35, or C36), with or without the functionalized polynucleotide (S9, S10), and with or without α-chymotrypsin, as indicated on top of each lane. Positive and negative controls are as in FIG. 12. NSKD-VI$_2$-NH$_2$ corresponds to NovaSyn KD resin bearing two spacers VI and an amino terminus group; TG-NH$_2$ corresponds to TentaGel resin bearing an amino terminus group.

The east (S9) and west (C34) components of the reaction cassette were prepared as shown in FIGS. 6 and 7 respectively. In semi-organic media, α-chymotrypsin catalyzes amide bond formation between Tyrosine methyl esters and a free amine. The reaction proceeds through the formation of an acyl-enzyme which in the semi-organic medium is attacked by the amine. (Wong, C.-H.; Whitesides, G. M. *Enzymes in Synthetic Organic Chemistry*; Baldwin, J. E., FRS; Magnus, P. D., FRS; (Eds.); Tetrahedron Organic Chemistry Series; Volume 12; Pergamon: Oxford; 1994.) FIG. 14 shows an agarose gel of the PCR products of 1 bead taken from the reaction of C34 (or C35) with 89 in the presence of α-chymotrypsin. When NovaSyn KD (C34) is used as the matrix, the background reaction overshadows the catalyzed reaction (FIG. 14, lanes 7–9). A control experiment with the resin alone (without the substrate portion) gives the same results which indicates that the background reaction is actually due to the adsorption of the polynucleotide onto the matrix, which cannot be eliminated completely even after extensive washing, but can be released in the PCR reaction media at high temperatures (lanes 1–3). With TentaGel based resins (C35), the background reaction could be eliminated after extensive washings (lanes 4–6). The reaction in the presence of the catalyst gave rise to a weaker band when compared to the background reaction (uncatalyzed amide bond formation), lanes 10–12. This trend is at variance with our expectations but can be explained as follows: a) α-chymotrypsin catalyzes the hydrolysis of the Tyrosine methyl ester of C34 (or C35), thus lowering the substrate concentration available to react with the polynucleotide-peptide conjugate. The uncatalyzed reaction gave a stronger signal (lane 10) because it is not hampered by this fact; b) α-chymotrypsin forms a stable acyl-enzyme intermediate with the most accessible sites, blocking the passage to the uncatalyzed reaction between the polynucleotide-peptide conjugate and the resin bound substrate.

Whatever the reason, it is disclosed herein that one can detect the slow-uncatalyzed peptide bond formation with encoded reaction cassette disclosed herein. At the same time, the encoded reaction cassette is disclosed to be able to detect the formation of chemical bonds. These results also show that with the present design, the size of the catalyst seems to handicap the methodology. For this reason, one can employ a chemically catalyzed bond formation using NaCNBH$_3$, as disclosed as follows.

Figure 8:
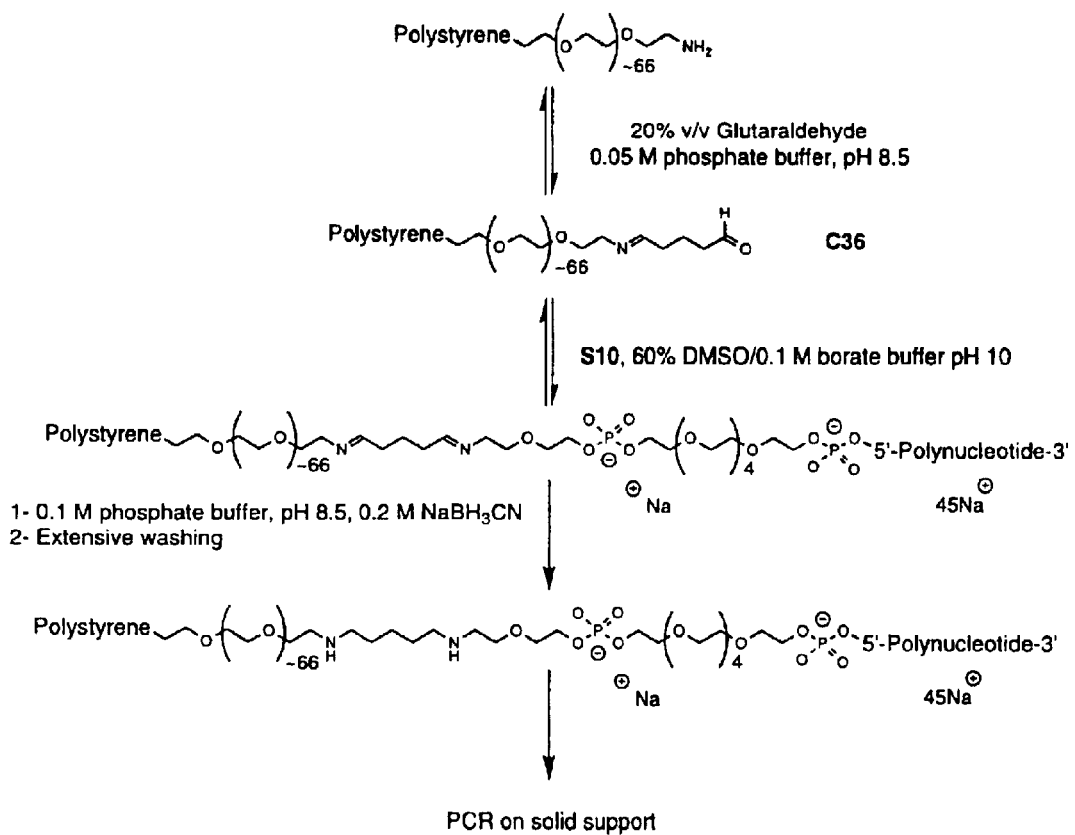
FIG. 8 illustrates the synthetic approach for the detection of chemically catalyzed bond formation: Coupling of the west side (C36) to the east side (S10) in a 60% DMSO/0.1 borate buffer pH 10 solution. The mixture is then reduced using sodiumcyanoborohydride, followed by extensive washing and then PCR amplication on a solid support with detection by a fluorescent assay.

Detection of Imine Bond Formation:

The synthetic scheme is shown in FIG. 8. We have used TentaGel for reasons discussed (vide supra). The matrix is first activated with glutaraldehyde and then coupled with 810 followed by NaCNBH$_3$ reduction. After extensive washing, one bead is submitted to the PCR. FIG. 14 shows an agarose gel that demonstrates the formation of the imine bond. The resin that was pre-treated with glutaraldehyde give rise to the 45-mer band (lane 13), whereas, as expected, the resin that was not submitted to this pre-treatment, did not give rise to the 45-mer (lane 14). Apart from its utility for the demonstration of the second part of the principle of the reaction cassette, this synthetic methodology may be used for the construction of an encoded library of reaction cassettes from a library of peptide-polynucleotide conjugates library that was obtained beforehand via an orthogonal synthetic scheme. The library thus obtained could be used in the bond cleavage detection mode.

Methods

Abbreviations:

DMTr (dimethoxytrityl), MMTr (monomethoxytrityl), Fmoc (fluorenylmethoxycarbonyl), Boc (tert-butyloxycarbonyl), DCM (dichloromethane), DMF (dimethylformamide), DMA (dimethylacetamide), ASWY (average stepwise yield), OAY (overall yield), DIEA (diisopropylethylamine), TBAF (tetrabutylammonium fluoride), THF (tetrahydrofurane), MeOH (methanol), dH$_2$O (distilled water), AcONa (sodium acetate), SPPS (solid phase peptide synthesis), t-Bu (tert-butyl), concd (concentrated), CPG (Controlled Pore Glass).

General

NMR spectra were recorded on a Bruker 300 MHz for $^1$H NMR and 500 MHz for $^{13}$C NMR, with the solvent as internal reference. All $^1$H and $^{13}$C NMR's in D$_2$O were performed with (2-methyl)$_2$-propanol as internal reference (C$\underline{H}_3$, 1.36 ppm; HOC(C$\underline{H}_3$)$_3$, 68.7 and 31.6 ppm). Melting points were measured on a Fisher-Johns Melting Point Apparatus. Chromatographic support was Silica flash Merck 60 (0.040–0.063 mm). The mass spectra were performed at the Mass Spectrometry Facility of The Scripps Research Institute.

Figure 4:
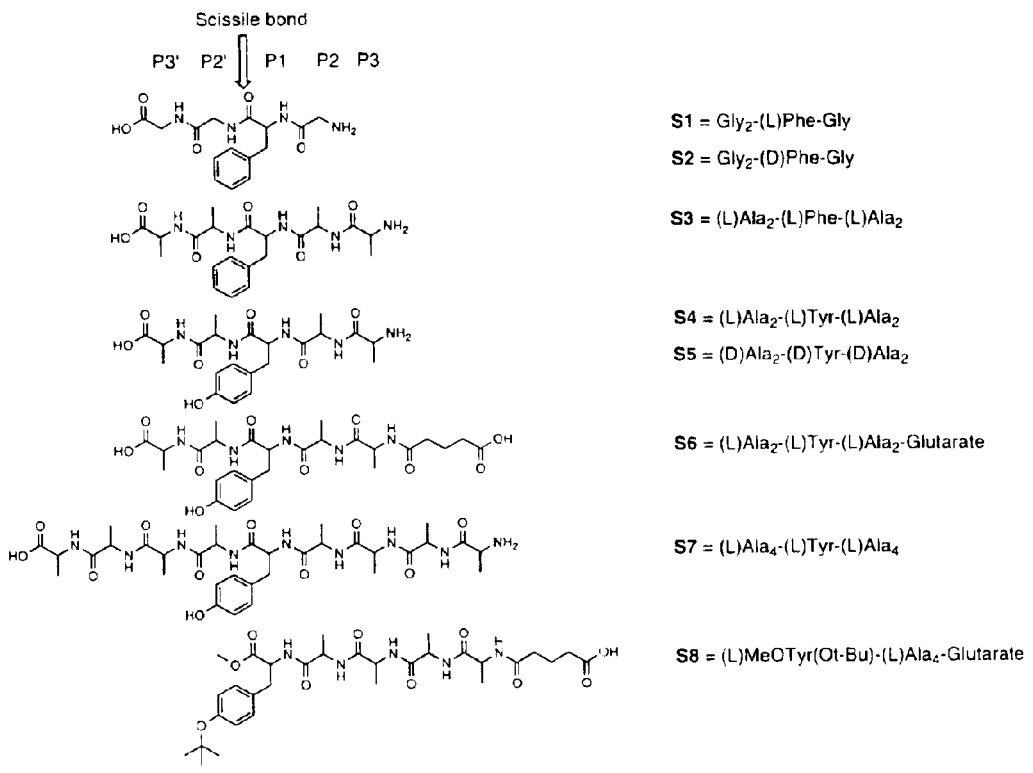
FIG. 4 illustrates the substrates studied in the detection of bond cleavage or formation (SEQ ID NOS. 1–6).

Synthesis of Substrates as Illustrated in FIG. 4:

Fmoc-Ala$_2$ and Fmoc-Tyr(OSit-BuMe$_2$) were synthesized according to a procedure described in: Atherton, A.; Sheppard, R. C. *Solid Phase Peptide Synthesis: A Practical Approach*; Oxford University Press: Oxford, 1989, pp. 47–53. See Supplementaary Material for Fmoc-Ala$_2$ and Fisher, P. M. *Tetrahedron Lett.* 1992, 33, 7605 for Fmoc-Tyr(OSit-BuMe$_2$). The other amino-acids, HBTU (O-benzotriazol-lyl-N,N,N',N'-tetramethyl-uronium hexafluorphosphate) and HOBt (1-hydroxybenzotriazole hydrate) are commercially available from Novabiochem; glutaric anhydride, DIEA (diisopropylethylamine), anhydrous DMA (dimethylamine) and DMF (dimethylformamide) from Aldrich; solvents (DCM (methylene chloride), MeOH (methanol), THF (tetrahydrofuran)) from Baxter were all HPLC (high performance liquid chromatography) grade with low water contents (<0.001%). Before use, the resins are preconditioned with 3% Cl$_3$CCO$_2$H/DCM treatment for 10 min followed by extensive DCM, DMF, 10% DIEA/DMF, DMF and DCM washes.

Synthesis of Substrates (S1–S7: SEQUENCE ID NO.'s 1–5) as Illustrated in FIG. 4:

The peptide substrates (S1–S7; SEQUENCE ID NO.'s 1–5) were assembled manually on either a 500 Å CPG (controlled pore glass) (~50 μmoles/g, Sigma or CPG Inc.), TentaGel-S-NH$_2$ support (~260 μmoles/g, Novabiochem or Rapp Polymere), or NovaSyn KD (~100 μmoles/g, Novabiochem) according to standard Fmoc and/or Boc methodologies (Stewart et al. *Solid Phase Peptide Synthesis*; Pierce Chemical Company: Rockford, Ill., 1984; Atherton et al. *Solid Phase Peptide Synthesis: A Practical Approach*, Oxford University Press: Oxford, 1989). To have a final loading of 40–60 μmoles/g, the first step of the synthesis is performed with an excess of solid support to amino acid monomer; after all the final washings, the unreacted amino groups are capped (0.25 volume of acetic anhydride 4.23 M in 2,6-lutidine; 0.75 volume of N,N-dimethylaminopyridine, 0.53 M in THF, 3 min). The same procedure of partial functionalization and capping applies for other loadings. The ASWY for peptide synthesis was 95–98%. After each coupling step the resin is washed with DMF, DCM and MeOH. The completion of the reaction is controlled with the Kaiser test (Kaiser et al. *Anal. Biochem.* 1970, 34, 595). The loading is determined when possible using either the DMTr (Dimethoxytrityl) cation assay (Gait et al. *Oligonucleotide Synthesis: A Practical Approach*; Oxford University Press: Oxford, 1990, p. 48 or the fulvene-piperidine adduct assay (Fmoc assay; $\epsilon_{302\,nm}$=7800 M$^{-1}$ cm$^{-1}$ in piperidine/DMF 20%; Atherton et al. *Solid Phase Peptide Synthesis: A Practical Approach*, Oxford University Press: Oxford, 1989).

The t-BuMe$_2$Si protecting group of the hydroxyl moiety on Tyrosine, as illustrated in FIG. 5, was removed at the end of the cassette assembly by treatment with 1 M TBAF in THF followed by extensive washing with THF, MeOH, dH$_2$O, tris-HCl buffer (20 mM, pH 8, NaCl 160 mM) and dH$_2$O. After this step the reaction cassette is ready for use in the bond cleavage detection mode.

The substrate S8 (SEQUENCE ID No. 6, FIG. 4) was prepared in 5 steps using standard solution phase peptide chemistry (vida infra). Since this compound tends to form a gel in fairly dilute solutions, its coupling either to TentaGel or NovaSyn KD was performed as follows: NovaSyn KD (0.5 g, 50 μmoles),) HBTU (50 mM)(O-benzotriazol-lyl-N, N,N',N'-tetramethyl-uronium hexafluorphosphate) and HOBt (50 mM)(1-hydroxybenzotriazole hydrate), DIEA (200 mM), S8 (SEQUNCE ID No. 6)(50 mM) in DMA (3 ml). The mixtures are shaken at 20° C. for 8-16 h. These conditions correspond to standard conditions diluted 2–4 times. The resin is then washed with DMA (dimethylamine), MeOH (methanol) and DCM (methylene chloride). Tyr(O-t-Bu) is deprotected with TFA/DCM (trifluoroacetic acid/methylene chloride) (1/4) for 10 min; the resin is washed with DCM, DMF, MeOH and DCM, and dried under high vacuum. The resin is now ready for use in bond formation detection in combination with the other part of the substrate as illustrated in FIG. 7. For TentaGel the coupling was performed as follows: TentaGel (0.25 g, 65 μmoles), HBTU (65 mM), HOBt (65 mM), S9 (SEQUNCE ID No. 6)(65 mM), DIEA (260 mM) in DMA (3 ml). Shake at 20° C. for 16 h. For the preparation of S9 (SEQUNCE ID No. 6) and S10 (FIG. 6) see DNA synthesis vida infra.

DNA Synthesis:

All monomers, reagents and solvents for DNA synthesis were purchased from Applied Biosystem (ABI) or Glen Research unless otherwise indicated. Expedite β-cyanoethyl phosphoramidites (Millipore) are protected with t-butylphenoxyacetyl on the amino groups of Adenine, Guanine, and Cytidine; Thymidine is not protected; the phosphate backbone generated with these monomers is protected as β-cyanoethyl ester. The phosphoramidite monomers used with a few of the second generation cassettes require incubation in concentrated ammonia in a sealed tube at 55° C. for 16–20 h. In order to minimize this exposure we used Expedite phosphoramidites with most of the reaction cassettes which allowed for rapid deprotection (1 hour at 55° C. in concd ammonia).

DNA synthesis was carried out on a 394 Applied Biosystem DNA Synthesizer using standard phosphoramidite chemistry (Gait et al. *Oligonucleotide Synthesis: A practical Approach*: Oxford University Press: New York, 1990). The standard 1 μmole cycle (termed Procedure A, 97 steps) was modified as described earlier for the synthesis on TentaGel (termed Procedure B, 97 steps as described in (Fenniri et al. *Proc. Natl. Acad. Sci. USA* 1995, 92, 2278). It was further modified in order to adapt it to both TentaGel and NovaSyn KD resins (termed Procedure C, 99 steps) as follows, in this order: a) DCM (methylene chloride) bottle (bottle 19) was replaced with anhydrous DMF; b) Cap A (bottle 11) was replaced by Expedite Cap A (Millipore); c) bottle 15 (iodine 0.1 M) was replaced by a less concentrated one (0.02 M); d) in the monitoring mode, step 77, 18 to column for 10 s, was replaced by 19 to column for 35 s; e) in the non-monitoring mode, one washing step was added, 19 to column for 35 s (step 80); f) in the non-monitoring mode, another washing step was added, 19 to column for 35 s (step 94); g) In the non-monitoring mode, steps 84, 87, and 90 were prolonged from 5 s to 10 s; h) all washing steps 3, 59, 61, 66, and 96 were prolonged from 10 s to 30 s; i) the incubation time with phosphoramidite and tetrazole (step 45) was prolonged from 25 s to 120 s; for the introduction of spacer VIII this step was extended to 900 s; j) the concentration of all monomers used on the DNA synthesis was 0.1 M in anhydrous acetonitrile; k) synthesis was monitored every 3 to 5 couplings.

The polynucleotide is deprotected upon treatment with concd NH$_3$ for 1 hour at 55° C. The DMTr group is removed upon treatment with 3% Cl$_3$CCO$_2$H in DCM (5 min), followed by extensive washing with DCM, THF, MeOH, tris-HCl buffer (20 mM, pH 8, NaCl 160 mM), and dH$_2$O. Tyrosine containing cassettes are treated for 15 min with 1 M TBAF in THF to remove the phenolic hydroxyl protecting group SiMe$_2$t-Bu and washed as above. After this step, the cassette is ready to use in the bond cleavage detection mode. Substrate S9 Used for the Detection of Enzymatic Catalyzed Bond Formation (FIG. 6):

For enzyme catalyzed bond formation detection, S9 was built on CPG 1000 Å (1 μmole scale) provided with a long chain alkylamino group bearing the first 21 methyl phosphoramidite as follows: Standard 1 μmole cycle (procedure A) of the 394 Applied Biosystem DNA synthesizer was used with methyl phosphoramidites and standard ABI reagents. After DNA synthesis, spacer VIII was introduced followed by spacer IX or X (Millipore). The MMTr amino-protecting group was removed upon treatment with 80% AcOH for 1 hour at 20° C. followed by washing with dH$_2$O, tris-HCl buffer (20 mM, pH 8, NaCl 160 mM), dH$_2$O, MeOH, DCM, and dried under high vacuum. The functionalized polynucleotide thus obtained is further derivatised with Fmoc-Ala$_2$ while still on the solid support following standard SPPS under the following concentration conditions: for 4 82 moles of resin bound polynucleotide, HBTU (25 mM), DIEA (100 mM), Fmoc-Ala$_2$ (25 mM), DMA (0.5 ml), shake at 20° C. for 2 h. The resin is washed with DMF, MeOH, DCM and dried under high vacuum. After this step the phosphate backbone is deprotected using a 1 mixture of thiophenol/Et$_3$N/dioxane (1/1/2) for 45 min and washed with dioxane and MeOH. The peptide-polynucleotide conjugate is detached from the resin and deprotected on the terminal Fmoc-amino acid group (1 hour in concentrated ammonia at 55° C.) and filtered through 0.8 μm disposable syringe filter (Corning). After this step, the polynucleotide-peptide conjugate is deprotected on the nucleobases upon treatment for 18 hours at 45–50° C. The solution is lyophilized and ethanol precipitated 3 times from 3 M AcONa pH 5.2 and used without further purification for enzyme catalyzed peptide coupling.

Substrate S10 Used for the Detection of Enzymatic Catalyzed Bond Formation (FIG. 6):

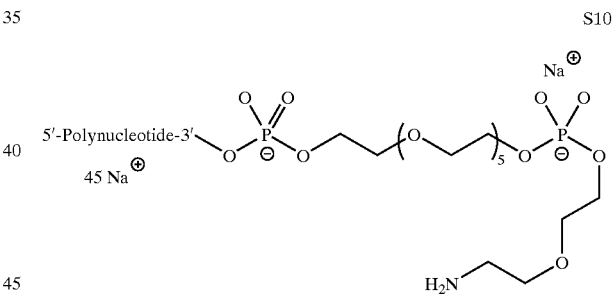

For detection of chemically catalyzed bond formation, S10 (the polynucleotide-VIII–IX (or polynucleotide-VIII–X) was assembled using 500 Å CPG, 1 μmole scale with Expedite β-cyanoethyl phosphoramidite monomers.

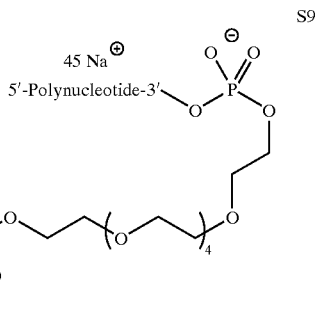

The terminal amino group is freed upon treatment with 80% AcOH for 1 hour at 20° C. followed by extensive washing with $dH_2O$, MeOH and $dH_2O$. The polynucleotide is deprotected upon treatment with concentrated ammonia for 1 hour at 55° C. The supernatant is recovered and lyophilised. The solid is ethanol precipitated 3 times from AcONa 3 M pH 5.2 and used without further purification for the coupling reaction.

Enzymatically Catalyzed Bond Cleavage (FIG. 5):

The cassette (0.01–10 mg, 5.9–30.1 μmoles/g) was suspended in 25 μl tris-HCl buffer (2 mM, pH 8, NaCl 16 mM) containing 1, $10^{-1}$, $10^{-2}$, $10^{-3}$, $10^{-4}$, $10^{-5}$, $10^{-6}$ or 0 units of α-chymotrypsin and the mixture was shaken at 20° C. Supernatant fluids (1–2 μl) were taken after 30 min. 1, 2, 3, 4, 12, 24 and 48 h, and were submitted to the PCR.

Enzymatically Catalyzed Bond Formation (FIG. 7):

then adapted to the MultiScreen Filtration System which allows the reaction to be stopped by applying vacuum to the device, followed by extensive washing with 0.1 M borate buffer pH 10, then 0.1 M phosphate buffer pH 8.5. 200 μl 0.2 M $NaCNBH_3$ in 0.1 M phosphate buffer, pH 8.5 was added to each well, and the plate was shaken for 3 hours at 20° C. and stored at 4° C. overnight without shaking. The liquid phase was filtered off the wells using the MultiScreen Filtration System, and the resin was washed extensively with $dH_2O$, 80% AcOH (2 5 10 min), $NH_3$ concd (2 5 10 min), TFA 2% (2 5 10 min), $NH_3$ concd (2 5 10 min), $dH_2O$ 80° C., and MeOH. One bead from each well was taken for PCR amplification.

PCR Experiments:

All the templates; SEQUENCE ID No.'s 8–14 (A–G, FIG. 9) and corresponding primers were custom made via

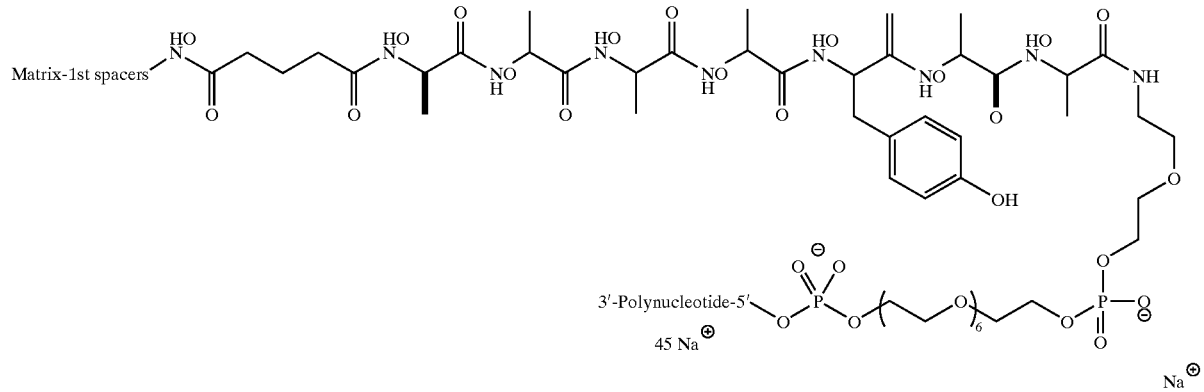

A few hundred beads (~5 mg) of C34 or C35 were placed in several wells of a 96-well filtration plate assembly (0.65 mm, Hydrophilic Durapore, Low Protein Affinity, Millipore) and were incubated with S9 (0.32 mM) in tris-HCl 100 mM pH 8/DMSO (40/60, final pH 8.75) in the presence of 1, 0.1, or 0 units of α-chymotrypsin (final volume 200 μl); the plate is shaken for 1 hour and is adapted to a MultiScreen Filtration System (Millipore) which allows the reaction to be stopped by applying vacuum to the device followed by extensive washings (DMSO/$dH_2O$ 60%, $dH_2O$, AcOH 80% (10 min), $dH_2O$, $NH_3$ concd (10 min), $dH_2O$, TFA 2% (10 min), $NH_3$ concd, $dH_2O$ 80° C., MeOH). One bead is taken from each well for PCR amplification.

Chemically Catalyzed Bond Formation (FIG. 8) Coupling of the West Side (C36 to the East Side (S10)):

Operon Corporation. For the reaction cassettes with template A (SEQUENCE ID No.1), aliquots (1 μl) from the reaction mixture were mixed with the PCR components: $MgCl_2$ 2.5 mM (Promega), 1.2 μl; Taq buffer (Promega), 2 μl; deoxynucleotide triphosphates 2.5 mM (Pharmacia), 1.6 μl; primer 1100 μmoles/μl, 1 μl; Primer II 100 μmoles/μl, 1 μl; $dH_2O$, 17.7 μl; Taq polymerase (Promega), 0.5 μl (2.5 U), was added just before starting the first PCR cycle. A positive control (PCR components only) was run with $dH_2O$ containing 1 μmole of the polynucleotide sequence used in this study. A negative control was run under the same conditions without the polynucleotide sequence. The PCR was run on a Perkin-Elmer-Cetus 9600 instrument with the following cycle program: denaturation 94° C., 30 s; annealing 55° C., 30 s; extension 72° C., 30 s. After 35 cycles the results were

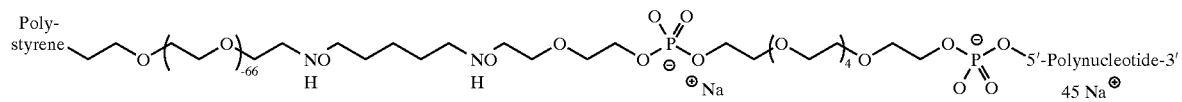

A few hundred beads of TentaGel (5 mg) were placed in several wells of a 96-well filtration plate assembly (0.65 mm, Hydrophilic Durapore, Low Protein Affinity, Millipore) and were incubated with 20% v/v glutaraldehyde/0.1 M phosphate buffer, pH 8.5. The plate was shaken at room temperature for 3 hours and then the beads extensively washed with $dH_2O$ and 0.1 M phosphate buffer, pH 8.5. The amino-functionalized polynucleotide S10 (0.15 mM) was added in 0.05 M borate buffer pH 10 containing 60% DMSO. The plate is shaken for 20 hours at 37° C., it was analysed on agarose gels [1% Gibco-BRL agarose, 2% FMC NuSieve GTG agarose with 90 mM Tris/64.6 mM borate/2.5 mM EDTA, pH 8.3 (15 TBE) at 103 mV]. For the reaction cassettes with template E (SEQUENCE ID No.13) (Table 4) we used HotWax low concentration $Mg^{++}$ beads (1.5 mM final concentration in a 50 μl final volume, Invitrogen); Taq buffer (Promega), 5 μl; dNTP 2.5 mM (Pharmacia), 4 μl; Primer 1100 μmoles/μl, 2.5 μl; Primer II 100 μmoles/μl, 2.5 μl; Taq polymerase (Promega) 1 μl (5 U); reaction supernatant fluid, 1 μl; $dH_2O$, 34 μl. The cycle program was preceded by a pre-heating step at 94° C. for 30 s and ended by an extension at 72° C. for 10 min. 35 Cycles were programmed as follows: denaturation 94° C., 30 s; annealing 49° C., 1 min; extension 72° C., 30 s. Negative and positive controls as well as analysis on agarose gel were performed as above. For bond formation detection, template F ((SEQUENCE ID No.14) was used as a Tag, and PCR conditions were identical to those described above with this template but with 25 cycles only.

Preparation of Spacer Molecules (Represented in Prior Art and/or Commercially Available Compounds):

The compounds I (Shaller et al. *J. Am. Chem. Soc.* 1963, 85, 3821), II (Nielsen et al. *Methods* 1994, 6, 361), Fmoc-Tyr(OSit-BuMe$_2$) (Fisher, P. M. *Tetrahedron Lett.* 1992, 33, 7605), 2; 21 (Morin et al. *Tetrahedron* 1992, 48, 9277), and 3; 22 (Prakash et al. *J. Chem. Soc. Perkin Trans.* 1 1991, 1273) are prepared according to previousely reported procedures. The compounds 19, 20, 23, 24, 25 and all the reagents and solvents are commercially available from Aldrich. Several attempts to derivatize 1, 5 and 9 with 19, 20, 21 or 22 under various conditions failed completely or gave only a poor yield of the desired product. In this section we describe the reaction that led to spacers III–VII in reasonably high yield (FIG. 3). The spacers IX (Glen Research) and X (Millipore Research) were commercially available.

Synthesis of 1-(tetrahydro-2H-pyran-2yloxy)-17-hydroxy-3,6,9,12,15-pentaoxahaptadecane (5) FIG. 3:

5

Compound 5: Compound 1 (25.0 g, 89 mMol; Sigma Chemical company), 3,4-dihydro-2H-pyran (7.5 g, 89 mMol; Aldrich), in methylene chloride (500 ml) were cooled to 0° C. and stirred with few drops of concentrated HCl for 1 h. The temperature was raised to 20° C. and the stirring was maintained overnight. Na$_2$CO$_3$ (3 g) was added and the suspension was stirred for 1 hour then filtered, followed by evaporation of the solvent to dryness and flash chromatography (SiO$_2$, ethylacetate/methylene chloride 0–100%) to afford compound 5 (C$_{17}$H$_{34}$O$_8$, 9.8 g, 30%) which was obtained as a viscous colorless oil. Rf=0.1 (SiO$_2$, ethyl acetate). $^1$H NMR (CDCl$_3$) δ: 4.56 (t, $^3$J(H,H)=2.9 Hz, 1H, OCHO); 3.9–3.3 (m, 28H, CH$_2$OCH$_2$ and C$\underline{H}_2$OH); 1.65–1.42 (m, 6H, CH$_2$CH$_2$CH$_2$ of THP). $^{13}$C NMR (CDCl$_3$) δ: 98.1 (OCHO); 72.1, 70.1, 70.0, 69.9, 69.8, 66.1, 61.5, 61.0, (CH$_2$OCH$_2$ and CH$_2$OH); 29.7, 24.5, 18.4 (C$\underline{H}_2$CH$_2$CH$_2$CH$_2$O). FAB+MS (NBA/NaI): 367 (M+H$^+$)/z; 389 (M+Na$^+$)/z.

Synthesis of 1-hydroxy-17-phtalimido-3,6,9,12,15-penatoxyheptadecane (9) FIG. 3:

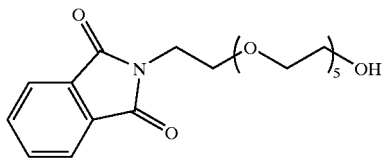

9

Compound 9: The compound 1 (25.0 g, 89 mMol; Sigma chemical company), phtalamide (12.9 g, 89 mMol), PPh$_3$ (23.0 g, 89 mMol) and anhydrous THF (450 ml, distilled over Na) were stirred at 20° C. under inert atmosphere. DEAD (15.3 g, 89 mMol; diethylazodicarboxylate is commercially available from Aldrich) in anhydrous THF (100 ml) was added dropwise over 2 hours at 20° C. and the reaction mixture was stirred overnight. The solvent was evaporated to dryness, the residue was taken in boiling dH$_2$O. After cooling down, the precipitate was filtered and the aqueous solution was evaporated to dryness under high vacuum. The viscous oil thus obtained was chromatographed (SiO$_2$ flash, EA/hexane 50–100%) yielding 9 as a colorless viscous oil (C$_{20}$H$_{29}$NO$_8$, 22.0 g, 60%). Rf=0.13 (SiO$_2$, EA). $^1$H NMR (CDCl$_3$) δ: 7.82 (m, 2H, Ar); 7.69 (m, 2H, Ar); 3.88 (t, $^3$J(H,H)=6.1 Hz, 2H, NCH$_2$); 3.72 (t, $^3$J(H,H)=5.4 Hz, 2H, NCH$_2$CH$_2$O); 3.69–3.54 (m, 22H, CH$_2$OCH$_2$ and C$\underline{H}_2$OH). $^{13}$C NMR (CDCl$_3$) δ: 167.9 (CO): 133.7, 131.7, 122.9 (Ar); 72.2, 70.3, 70.2, 70.1, 70.0, 69.95, 69.7 (OCH$_2$CH$_2$O); 67.5 (OC$\underline{H}_2$CH$_2$N); 61.2 (OCH$_2$ C$\underline{H}_2$OH); 36.9 (C$\underline{H}_2$N).

FAB+MS (NBA/NaI): Expected exact mass for (M+H$^+$)/z 412.1971, observed 412.1983; 434 (M+Na$^+$)/z.

Synthesis of 1-phtalimido-17-[(4,4'-bismethoxytrityl)-oxy]-3,6,9,12,15-pentaoxaheptadecane (121 FIG. 3:

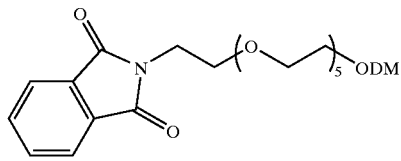

12

Compound 12: Compound 9 (1.8 g, 4.4 mMol), DMTrCl (4,4 dimethoxytrityl chloride is commercially available from Aldrich) (2.2 g, 6.6 mMol) were stirred in pyridine (20 ml) for 40 hours at 20° C. Et$_3$N (12 mMol, triethyl amine) was added and the solvent was evaporated to dryness. 12 (C$_{41}$H$_{47}$NO$_{10}$, 2.8 g, 88%) was obtained after flash chromatography (SiO$_2$, EA/DCM 0–50%) as a yellow viscous oil. Rf=0.15 AU (SiO$_2$, EA/hexane 50%). $^1$H NMR (CDCl$_3$) δ: 7.83 (m, 2H, phtalimide); 7.68 (m, 2H, phtalimide); 7.47 (d, $^3$J(H,H)=7.1 Hz, 2H, Ph DMTr); 7.34 (d, $^3$J(H,H)=8.9 Hz, 4H, p-MeOPh DMTr). 7.26 (t, $^3$J(H,H) 7.6 Hz, 2H, Ph DMTr); 7.18 (t, $^3$J(H,H)=7.3 Hz, 1H, Ph DMTr); 6.81 (d, $^3$J(H,H)=8.9 Hz, 4H, p-MeOPh DMTr); 3.88 (t, $^3$J(H,H). =5.9 Hz, 2H, CH$_2$N); 3.77 (s, 6H, CH$_3$O); 3.75–3.5 (m, 20H, CH$_2$OCH$_2$); 3.21 (t, $^3$J(H,H)=5.4 Hz, 2H, CH$_2$ODMTr). $^{13}$C NMR (CDCl$_3$) δ: 168.2 (CO); 158.3, 145.0, 136.3, 130.0, 128.1, 127.7, 126.6, 123.2, 113.0 (DMTr Ar); 133.9, 132.2, 123.2 (phtalimide Ar); 85.8 ((p-MeOPh)$_2$PhC$\underline{O}$); 70.7, 70.6, 70.55, 70.5, 70.45, 70.0, 67.8 (CH$_2$OCH$_2$); 63.1 (CH$_2$ODMTr); 55.1 (CH$_3$O); 37.2 (CH$_2$N). FAB+MS (NBA/NaI): Expected exact mass for (M+Na$^+$)/z 736;3098, observed 736.3123.

Synthesis of 1-amino-17-[(4,4'-bismethoxytrityl)oxy]-3,6,9,12,15-pentaoxaheptadecane (III) FIG. 3:

III

Compound III: Compound 12 (1.7 g, 2.3 mMol), (NH$_2$)$_2$ (hydrazine) (23.4 mMol, 0.73 ml) and EtOH (100 ml) were refluxed for 3 h. After cooling down, the precipitate was filtered and the solvent evaporated to dryness. The residual oil was taken in diethylether and the precipitate was filtered off. The organic phase was evaporated to dryness yielding III (C$_{33}$H$_{45}$NO$_8$, 1.2 g, 89%) as a viscous pale yellow oil which was used without further purification. $^1$H NMR (CDCl$_3$) δ: 7.45 (d, $^3$J(H,H)=7.3 Hz, 2H, Ph DMTr); 7.33 (d, $^3$J(H,H)= 8.8 Hz, 4H, p-MeOPh DMTr); 7.27 (t, $^3$J(H,H)=7.0 Hz, 2H, Ph DMTr); 7.18 (t, $^3$J(H,H)=7.0 Hz, 1H, Ph DMTr); 6.81 (d, $^3$J(H,H)=8.8 Hz, 4H, p-MeOPh DMTr); 3.77 (s, 6H, CH$_3$O); 3.73–3.59 (m, 18H, OCH$_2$CH$_2$O); 3.48 (t, $^3$J(H,H)=5.1 Hz, 2H, C$\underline{H}_2$CH$_2$NH$_2$); 3.21 (t, $^3$J(H,H)=5.2 Hz, 2H, CH$_2$ODMTr); 2.84 (t, $^3$J(H,H)=5.1 Hz, 2H, CH$_2$C$\underline{H}_2$NH$_2$). $^{13}$C NMR (CDCl$_3$) δ: 158.3, 145.0, 136.3, 130.0, 128.1, 127.7, 126.6, 113.0 (Ar); 85.8 ((p-MeOPh)$_2$PhC̲O); 73.4, 70.7, 70.6, 70.5, 70.2 (CH$_2$OCH$_2$); 63.1 (CH$_2$ODMTr); 55.2 (CH$_3$O); 41.7 (CH$_2$NH$_2$).

FAB+MS (NBA/NaI): 584 (M+H$^+$)/z; expected exact mass for (M+Na$^+$)/z 606.3043, observed 606.3072.

Synthesis of 1-hydroxy-17-[(4,4'-bismethoxytrityl)oxy]-3,6,9,12,15-pentaoxaheptadecane (13) (Formed in Step i. FIG. 3: Compound is an Intermediate and Not Shown):

Compound 13: Compound 1 (5 g, 17.7 mMol) and DMTrCl dimethoxytrityl chloride (6.3 g, 17.7 mMol) were stirred in pyridine (17 ml) under inert atmosphere at 20° C. for 48 h. Et$_3$N (4 ml) was added and the solvent was evaporated to dryness. The oily residue thus obtained was taken in ether (100 ml) and extracted with dH$_2$O (100 ml). The organic layer was dried over Na$_2$SO$_4$, filtered, evaporated to dryness, and dried under high vacuum. 13 (C$_{33}$H$_{14}$O$_9$, 3.3 g, 32%) was obtained as a yellow oil after flash chromatography (SiO$_2$, EA/hexane 50–100%). Rf=0.12 (SiO$_2$, EA). $^1$H NMR (CDCl$_3$ filtered on basic Al$_2$O$_3$) δ: 7.46 (d, $^3$J(,H,H)=7.2 Hz, 2H, Ph DMTr); 7.34 (d, $^3$J(H,H)=8.8 Hz, 4H, p-MeOPh DMTr); 7.27 (t, $^3$J(H,H)=7.8 Hz, 2H, Ph DMTr); 7.19 (t, $^3$J(H,H)=7.2 Hz, 1H, Ph DMTr); 6.82 (d, $^3$J(H,H)=8.9 Hz, 4H, p-MeOPh DMTr); 3.78 (s, 6H, CH$_3$O); 3.7–3.57 (m, 22H, CH$_2$OCH$_2$ and CH$_2$OH); 3.22 (t, $^3$J(H,H)=5.3 Hz, 2H, CH$_2$ODMTr). $^{13}$C NMR (CDCl$_3$ filtered on basic Al$_2$O$_3$) δ: 158.3, 145.1, 136.3, 130.1, 128.2, 127.7, 126.6, 113.0 (Ar); 85.9 ((p-MeOPh)$_2$PhC̲O); 72.5, 70.7, 70.68, 70.65, 70.62, 70.58, 70.52, 70.48, 70.45, 70.42, 70.3 (CH$_2$OCH$_2$); 63.1 (CH$_2$ODMTr); 61.7 (CH$_2$OH); 55.2 (CH$_3$O).

FAB+MS (NBA/CsI): expected exact mass for (M+Cs$^+$)/z 717.2040, observed 717.2022.

Synthesis of 1,17-bis[(p-toluenesulfonyl)oxy]-3,6,9,12,15-pentaoxaheptadecane (14) (Step 'k' FIG. 3: Compound is an Intermediate and Not Shown):

Compound 14: Compound 1 (25.0 g, 89 mMol), p-toluenesulfonyl chloride (50.9 g, 267 mMol) were stirred in dry pyridine (75 ml) under inert atmosphere at 0° C. for 4 h. The reaction media was then poured on ice (800 ml) and stirred vigorously. DCM (300 ml) was added and the aqueous layer was carefully acidified to pH 1 with 3 M HCl. The aqueous layer was further extracted with DCM (2 5 300 ml) and the organic layers were combined and extracted with saturated NH$_4$Cl (2 5 300 ml), dH$_2$O (2 5 300 ml), dried over MgSO$_4$, filtered, evaporated to dryness, and the residual oil was dried under high vacuum. After flash chromatography (SiO$_2$' MeOH/DCM 0–1%) 14 was obtained as a viscous colorless oil (C$_{26}$H$_{38}$S$_2$O$_9$, 40 g, 76%). Rf=0.49 (SiO$_2$, EA).

$^1$H NMR (CDCl$_3$) δ: 7.75 (d, $^3$J(H,H)=8.3 Hz, 4H, Ar); 7.31 (d, $^3$J(H,H) 8.1 Hz, 4H, Ar); 4.10 (t, $^3$J(H,H)=4.7 Hz, 4H, CH$_2$OTs); 3.65–3.53 (m, 20H, CH$_2$OCH$_2$); 2.40 (s, 6H, CH$_3$ Ts). $^{13}$C NMR (CDCl$_3$) a: 144.7, 132.7, 129.7, 127.8 (Ar); 77.0, 76.8, 71.2, 70.5, 70.4, 70.3, 69.2, 68.5 (CH$_2$O); 21.5 (CH$_3$ Ts). FAB+MS (NBA/NaI): expected exact mass for (M+Na$^+$)/z 613.1753, observed 613.1740.

Synthesis of 1,27-bis-(hydroxy)-5,8,11,14,17,20,23-heptaoxaheptadodecane (15) (Step 'l' FIG. 3: Compound is an Intermediate and Not Shown):

Compound 15: Compound 23 (146.5 g, 1.63 Mol; Aldrich company) and Na (5.1 g, 0.22 Mol) were stirred at 20° C. under inert atmosphere then heated to 65° C. until the complete dissolution of Na. The mixture was further stirred for 2 hours at 45° C. then transferred through a canular to a solution of 14 (60.0 g, 0.102 Mol) in THF (240 ml). Because of the high viscosity of the 23/Na solution it was kept and transferred at 65° C., while the 14/THF solution was cooled to 0° C. After the transfer was completed (1 h), the temperature was kept at 0° C. for 3 hours then overnight at 20° C. The reaction was quenched with a saturated solution of NH$_4$Cl (250 ml), THF was evaporated and the remaining aqueous layer was extracted with DCM (3 5 250 ml), dried over MgSO$_4$, filtered, and evaporated to dryness. The pure compound 15 (C$_{20}$H$_{42}$O$_9$, 25.2 g, 58%) was obtained as a viscous colorless oil after flash chromatography (SiO$_{21}$ MeOH/EA 0–10%). Rf=0.17 (SiO$_{21}$ MeOH/EA). $^1$H NMR (CDCl$_3$) δ: 3.61–3.52 (m, 28H, CH$_2$OCH$_2$); 3.45 (t, $^3$J(H, H)=6.0 Hz, 4H, C$\underline{H}_2$OH); 1.59 (m, 8H, C$\underline{H}_2$C$\underline{H}_2$CH$_2$OH). $^{13}$C NMR (CDCl$_3$) δ: 71.2, 71.1, 70.4, 70.3, 70.25, 70.2, 69.9 (CH$_2$OCH$_2$); 62.2 (CH$_2$OH); 29.8, 26.4 (C$\underline{H}_2$C H$_2$CH$_2$OH). FAB+MS (NBA/NaI): expected exact mass for (M+Na$^+$)/z 449.2727, observed 449.2738.

Synthesis of 1-phtalimido-27-hydroxy-5,8,11,14,17,20,23-heptaoxaheptadodecane (16):

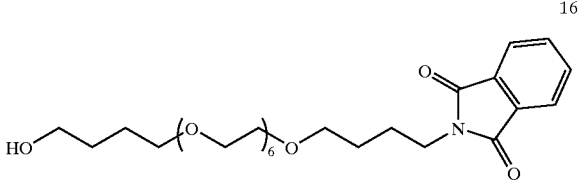

16

Compound 16: Compound 15 (23.6 g, 55.3 mMol), phtalamide (6.3 g, 42.5 mMol), PPh$_3$ (11.2 g, 42.5 mMol) and anhydrous THF (290 ml, distilled over Na) were stirred under inert atmosphere. DEAD diethyl-azodicarboxylate (7.4 g, 42.5 mMol) in anhydrous THF (50 ml) was added slowly using a syringe pump (8.4 ml/h) at 20° C. After the addition was complete the reaction mixture was stirred at 20° C. overnight. The solvent was evaporated to dryness and the residual solid was taken in boiling dH$_2$O. After cooling down, the precipitate was filtered and the aqueous solution was evaporated to dryness under high vacuum. The oil thus obtained was chromatographed (SiO$_2$ flash, a) DCM, b) MeOH/EA 0–10%) yielding 16 as a colorless viscous oil (C$_{28}$H$_{45}$NO$_{10}$, 11.6 g, 95.2% based on recovered 15). Rf=0.1 (SiO$_2$, MeOH/EA 2%). $^1$H NMR (CDCl$_3$) δ: 7.81 (m, 2H, Ar); 7.70 (m, 2H, Ar); 3.69 (t, $^3$J(H,H)=6.9 Hz, 2H, CH$_2$N); 3.63–3.45 (m, 30H, CH$_2$OCH$_2$ and CH$_2$OH); 1.74–1.60 (m, 8H, C$\underline{H}_2$C$\underline{H}_6$CH$_2$O). $^{13}$C NMR (CDCl$_3$) δ: 168.4 (CO); 133.9, 132.1, 123.1 (Ar); 71.3, 70.6, 70.5, 70.4, 70.1, 70.0 (CH$_2$OCH$_2$); 62.6 (CH$_2$OH); 37.7 (CH$_2$N); 30.2, 26.9, 26.6, 25.3 (C$\underline{H}_2$C$\underline{H}_2$CH$_2$O). FAB+MS (NBA/NaI): 556 (M+H$^+$)/z; expected exact mass for (M+Na$^+$)/z 578.2941, observed 578.2963.

Synthesis of 1-phtalimido-27-[(4,4'-bismethoxytrityl)oxy]-5,8,11,14,17,20,23-heptaoxaheptadodecane (17) (Step 'i' FIG. 3: Compound 17 is an Intermediate and is Therefore Not Shown):

Compound 17: Compound 16 (1.4 g, 2.57 mMol) and DMTrCl (1.74 g, 5.1 mMol) in pyridine (10 ml) were stirred at 20° C. for 48 h. Et$_3$N (1 ml) was added and the solvent was evaporated to dryness. The oily residue thus obtained was taken in DCM (20 ml) and extracted with dH$_2$O (2 5 20 ml). The organic layer was dried over Na$_2$SO$_4$, filtered, and evaporated to dryness, and dried under high vacuum. 17 (C$_{49}$H$_{63}$O$_{12}$N, 1.9 g, 86%) was obtained as a pale yellow oil after flash chromatography (SiO$_2$, EA/hexane 50–75%).

Rf=0.33 (SiO$_2$, EA). $^1$H NMR (CDCl$_3$) δ: 7.84 (m, 2H, phtalimide); 7.71 (m, 2H, phtalimide); 7.44 (d, $^3$J(H,H)=7.2 Hz, 2H, Ph DMTr); 7.32 (d, $^3$J(H,H) 8.8 Hz, 4H, p-MeOPh DMTr); 7.28 (t, $^3$J(H,H)=7.7 Hz, 2H, Ph DMTr); 7.20 (t, $^3$J(H,H)=7.1 Hz, 1H, Ph DMTr); 6.82 (d, $^3$J(H,H)=8.8 Hz, 4H, p-MeOPh DMTr); 3.79 (s, 6H, CH$_3$O); 3.71 (t, $^3$J(,H, H)=6.9 Hz, 2H, CH$_2$N); 3.64–3.42 (m, 28H, CH$_2$OCH$_2$); 3.06 (t, $^3$J(H,H)=5.9 Hz, 2H, CH$_2$ODMTr); 1.80–1.59 (m, 8H, CH$_2$CH$_2$CH$_2$O). $^{13}$C NMR (CDCl$_3$) δ: 168.5 (CO); 158.2, 145.3, 136.6, 130.0, 128.2, 127.7, 126.5, 112.9 (DMTr Ar); 133.9, 132.1, 123.2 (phtalimide Ar); 85.8 ((p-MeOPh)$_2$PhHO); 71.3, 70.6, 70.55, 70.2, 70.0 (CH$_2$OCH$_2$); 63.0 (CH$_2$ODMTr); 55.2 (CH$_3$O); 37.7 (CH$_2$N); 26.9, 26.7, 26.6, 25.3 (CH$_2$CH$_2$CH$_2$O). FAB+MS (NBA/CsI): expected exact mass for (M+Cs$^+$)/z 990.3405, observed 990.3382.

Synthesis of 1-amino-27-[(4,4″-bismethoxytrityl)oxy]-5,8,11,14,17,20,23-heptaoxaheptadodecane (IV) FIG. 3 Step j:

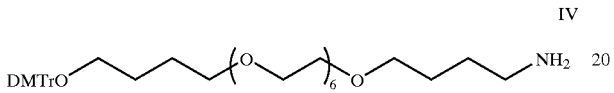

IV

Compound (IV): Compound 17 (1.1 g, 2.3 mMol), (NH$_2$)$_2$ (0.4 ml, 12.8 mMol) and EtOH (40 ml) were refluxed for 2 h. After cooling down the precipitate was filtered and the solvent evaporated to dryness. The residual oil was taken in diethylether and the precipitate was filtered off. The organic phase was evaporated to dryness yielding IV (C$_{41}$H$_{61}$NO$_{10}$, 0.85 g, 91%) which was used in the next step without further purification.

$^1$H NMR (CDCl$_3$) δ: 7.44 (d, $^3$J(H,H)=7.1 Hz, 2H, Ph DMTr); 7.32 (d, $^3$J(H,H)=8.9 Hz, 4H, p-MeOPh DMTr); 7.28 (t, $^3$J(H,H)=7.4 Hz, 2H, Ph DMTr); 7.20 (t, $^3$J(H,H)=7.1 Hz, 1H, Ph DMTr); 6.82 (d, $^3$J(H,H)=8.9 Hz, 4H, p-MeOPh DMTr); 3.79 (s, 6H, CH$_3$O); 3.65–3.40 (m, 28H, CH$_2$OCH$_2$); 3.05 (t, $^3$J(H,H)=6.0 Hz, 2H, CH$_2$ODMTr); 2.70 (t, $^3$J(H,H)=6.5 Hz, 2H, CH$_2$NH$_2$); 1.7–1.45 (m, 8H, CH$_2$CH$_2$CH$_2$O). $^{13}$C NMR (CDCl$_3$) δ: 158.2, 145.3, 136.6, 130.0, 128.1, 127.7, 126.5, 112.9 (Ar); 85.6 ((p-MeOPh)$_2$Ph CO); 71.3, 71.2, 70.5, 70.1, 70.0 (CH$_2$OCH$_2$); 63.0 (CH$_2$ODMTr); 55.2 (CH$_3$O); 42.0 (CH$_2$NH$_2$); 30.4, 27.0, 26.6, 26.5 (CH$_2$CH$_2$CH$_2$O). FAB+MS (NBA/CsI): expected exact mass for (M+H$^+$)/z 728.4374, observed 728.4351; 860 (M+Cs$^+$)/z.

Synthesis of 27-phtalimido-5,8,11,14,17,20,23-heptaoxaheptadodecanoic acid (V) FIG. 3 Step m:

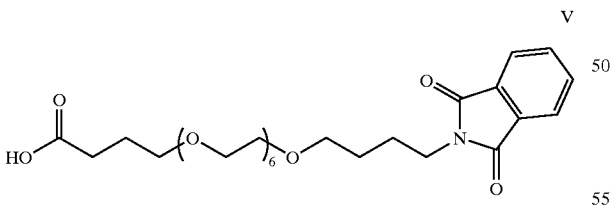

V

Compound (V): Compound 16 (8.6 g, 15.5 mMol) and pyridinium dichromate (29.2 g, 77.5 mMol) were stirred in DMF (145 ml) under inert atmosphere at 20° C. for 12 h. dH$_2$O (1500 ml) was added and the reaction media was extracted with DCM (4 5 1500 ml). The organic layers were combined and evaporated to 500 ml final volume, dried over MgSO$_4$, filtered, and evaporated to dryness. The residue was taken in diethylether (500 ml) and filtered on celite to remove the insoluble materials. The oil obtained after evaporation of the solvent was chromatographed (SiO$_2$ flash, MeOH/EA 0–10%) yielding pure V as a colorless viscous oil (C$_{29}$H$_{43}$NO$_{11}$, 7.2 g, 82%). Rf=0.4 (SiO$_2$, MeOH/EA 10%). $^1$H NMR (CDCl$_3$) δ: 7.82 (m, 2H, Ar); 7.70 (m, 2H, Ar); 3.67 (t, J(H,H)=6.9 Hz, 2H, J CH$_2$N); 3.62–3.44 (m, 28H, CH$_2$OCH$_2$); 2.41 (t, $^3$J(H,H)=7.2 Hz, 2H, CH$_2$CO$_2$H); 1.87 (m, 2H, CH$_2$CH$_2$CO$_2$H); 1.71 (m, 2H, NCH$_2$CH$_2$); 1.61 (m, 2H, NCH$_2$CH$_2$CH$_2$). $^{13}$C NMR (CDCl$_3$) δ: 176.8 (CO$_2$H); 168.4 (CO); 133.9, 132.1, 123.2 (Ar); 70.6, 70.5, 70.1 (CH$_2$OCH$_2$); 37.7 (CH$_2$N); 31.0 (CH$_2$CO$_2$H); 26.9 ( CH$_2$CH$_2$CO$_2$H); 25.3, 24.8 (CH$_2$CH$_2$CH$_2$N). FAB+MS (NBA/NaI): 570 (M+H$^+$)/z; expected exact mass for (M+Na$^+$)/z 592.2734, observed 592.2748; 614 (M–H$^+$ 2Na$^+$)/z.

Synthesis of 27-amino-5,8,11,14,17,20,23-heptaoxaheptadodecanoic acid (18) FIG. 3. Step j:

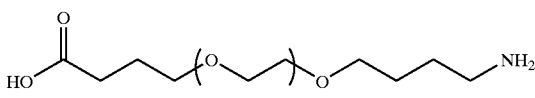

18

Compound 18: Compound V (2.7 g, 4.7 mMol), (NH$_2$)$_2$ hydrazine (1.5 ml, 48.0 mMol) and EtOH (120 ml) were refluxed for 3 h. After cooling down (1 h), the precipitate was filtered and the solvent evaporated to dryness. The residual oil was taken in 1 M HCl, filtered on paper, evaporated to dryness and dried under high vacuum. It was then taken in MeOH/diethylether 30%, filtered and evaporated to dryness yielding 18 in the hydrochloride salt form (C$_{20}$H$_{42}$NO$_9$Cl, 2.0 g, 89.4%). This compound can be further purified on a Dowex AG1X8 (OH$^-$) and eluted with 1 M HCl if the starting material (V) was not carefully purified. $^1$H NMR (D$_2$O) δ: 3.82–3.72 (m, 24H, OCH$_2$CH$_2$O); 3.70–3.66 (m, 4H, CH$_2$CH$_2$CH$_2$O); 3.15 (t, $^3$J(H,H)=6.6 Hz, 2H, CH$_2$NH$_3$Cl); 2.58 (t, $^3$J(H,H)=7.4 Hz, 2H, CH$_2$CO$_2$H); 2.03 (m, 2H, CH$_2$CH$_2$CO$_2$H); 1.85 (m, 4H, CH$_2$C H$_2$CH$_2$NH$_3$Cl). $^{13}$C NMR (D$_2$O) δ: 184.2 (CO$_2$H); 72.1, 71.8, 71.5, 71.1 (CH$_2$OCH$_2$); 41.2 (CH$_2$NH$_3$Cl); 32.5 ( CH$_2$CO$_2$H); 27.6 (CH$_2$CH$_2$CO$_2$H); 26.0, 25.7 (CH$_2$C H$_2$CH$_2$NH$_3$Cl) FAB+MS (NBA): expected exact mass for (M–Cl$^-$)/z 440.2860, observed 440.2850.

Synthesis of 27-Fmoc-amido-5,8,11,14,17,20,23-heptaoxaheptadodecanoic acid (VI) FIG. 3. Step n:

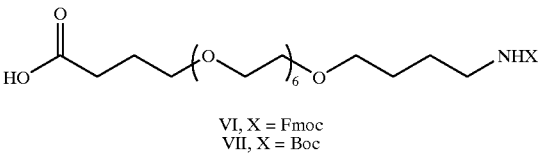

VI, X = Fmoc
VII, X = Boc

The hydrochloride salt of 18 (1.0 g, 2.1 mMol) and 10% Na$_2$CO$_3$ (7.8 ml, 7.4 mMol) were stirred in dioxane (5.7 ml) and dH$_2$O (7.4 ml) at 0° C. FmocCl (0.6 g, 2.3 mMol) in dioxane (5.7 ml) was added dropwise over 15 min. The temperature was kept at +4° C. for an additional 4 hours and 1 hour at 20° C. 0.01 M HCl (135 ml) was added, and the mixture was extracted with DCM (3 5 70 ml). The organic layers were dried over MgSO$_4$, filtered, and evaporated to dryness under reduced pressure. After flash chromatography (SiO$_2$, EA), VI (C$_{35}$H$_{51}$NO$_{11}$, 1.2 g, 87%) was obtained as a pure viscous colorless oil. Rf=0.2 (S102, EA). $^1$H NMR (CDCl$_3$) δ: 7.79 (d, $^3$J(H,H) 7.4 Hz, 2H, Ar); 7.63 (d, $^3$J(H,H)=7.4 Hz, 2H, Ar); 7.42 (t, $^3$J(H,H)=7.3 Hz, 2H, Ar); 7.34 (t, $^3$J(H,H)=7.4 Hz, 2H, Ar); 5.23 (t, $^3$J(H,H)=5.3 Hz, 1H, OCONH); 4.43 (d, $^3$J(H,H)=6.8 Hz, 2H, CH$_2$OCONH); 4.24 (t, $^3$J(H,H)=6.7 Hz, 1H, CHCH$_2$OCONH); 3.70–3.45

(m, 28H, CH$_2$OCH$_2$); 3.26 (m, 2H, OCONHCH$_2$); 2.43 (t, $^3$J(H,H)=7.4 Hz, 2H, CH$_2$CO$_2$H); 1.92 (m, 2H, CH$_2$CH$_2$CO$_2$H); 1.63 (m, 4H, NCH$_2$CH$_2$CH$_2$). $^{13}$C NMR (CDCl$_3$) δ: 173.9 (CO$_2$H); 156.4 (OCONH); 143.9, 141.2, 127.5, 127.0, 125.0, 119.8 (Ar); 70.8, 70.5, 70.0, 66.2 (CH$_2$OCH$_2$); 51.5 (CHCH$_2$OCONH); 47.2 (CH CH$_2$OCONH); 40.7 (OCONHCH$_2$); 30.6 (CH$_2$CO$_2$H); 26.7 (CH$_2$CH$_2$CO$_2$H); 26.6, 24.8 (OCONHCH$_2$CH$_2$CH$_2$). FAB+ MS (NBA/CsI): expected exact mass for (M+Cs$^+$)/z 794.2516, observed 794.2527.

Synthesis of 27-Boc-amido-5,8,11,14,17,20,23-heptaoxaheptadodecanoic acid (VII) FIG. 3. Step o:

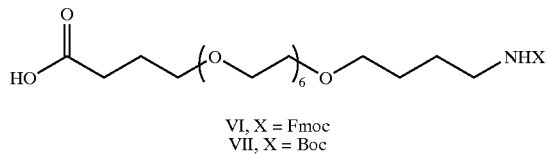

VI, X = Fmoc
VII, X = Boc

The hydrochloride salt of 16 (0.84 g, 1.76 mMol) and Et$_3$N (1.0 ml, 7.3 mMol) were stirred in DMF (20 ml) under inert atmosphere at 0C. Boc$_2$O (0.46 g, 2.1 mMol) in DMF (10 ml) was added dropwise over 15 min. The temperature was raised to 20° C. and the mixture was stirred for an additional 3 h. dH$_2$O (4 ml) was added to destroy excess Boc$_2$O and the solvent was evaporated to dryness under high vacuum. The residual oil was taken in 0.01 M HCl (25 ml) and extracted with ethylacetate (3 5 25 ml). The organic layers were combined and dried over MgSO$_4$, filtered and evaporated to dryness. After flash chromatography (SiO$_2$, EA), VII (C$_{25}$H$_{49}$NO$_{11}$, 0.9 g, 84%) was obtained as a pure viscous colorless oil. Rf=0.26 (SiO$_2$, MeOH/DCM 10%). $^1$H NMR (CDCl$_3$) δ: 3.70–3.40 (m, 28H, CH$_2$OCH$_2$); 3.09 (m, 2H, CH$_2$NHCO); 2.42 (t, $^3$J(H,H)=7.1 Hz, 2H, CH$_2$CO$_2$H); 1.88 (m, 2H, CH$_2$CH$_2$CO$_2$H); 1.55 (m, 4H, CONHCH$_2$C H$_2$CH$_2$); 1.41 (s, 9H, (CH$_3$)$_3$C).

$^{13}$C NMR (CDCl$_3$) δ: 176.9 (CO$_2$H); 156.0 (OCONH); 70.8, 70.5, 70.4, 70.0, 69.9 (CH$_2$OCH$_2$ and (CH$_3$)$_3$C); 40.2 (OCONHCH$_2$); 30.8 (CH$_2$CO$_2$H); 28.3 (CH$_3$)$_3$C); 26.7, 26.65 (OCONHCH$_2$CH$_2$CH$_2$); 24.8 (CH$_2$CH$_2$CO$_2$H). FAB+MS (NBA/CsI): expected exact mass for (M+Cs$^+$)/z 672.2360, observed 672.2385; 804 (M−H$^+$+2Cs$^+$)/z.

FAB+MS (NBA): expected exact mass for (M+H)/z 540.3384, observed 540.3405.

Synthesis of Fmoc-Ala$_2$ Intermediate for (S8) as Illustrated in FIG. 4:

This compound was prepared according to a procedure as described in Atherton et al. *Solid Phase Peptide Synthesis: A Practical Approach*; Oxford University Press: Oxford, 1989, pp. 47–53. The typical procedure is as follows: H$_2$NAla$_2$OH (5.0 g, 31.2 mMol; commercially available from Sigma) and 10% Na$_2$CO$_3$ (83 ml, 78.0 mMol) were stirred in dioxane (55 ml) and dH$_2$O (57 ml) at 0° C. FmocCl (9-fluorenylmethyl chloroformate) (8.5 g, 32.8 mMol; Aldrich chemical company) in dioxane (55 ml) was added dropwise over 30 min. The temperature was maintained at 0° C. for 1 hour and at 20° C. for 1 h. The precipitate that appeared during the course of the reaction was dissolved by adding dH$_2$O (360 ml) and dioxane (210 ml) followed by stirring at 20° C. for 1 h. The reaction medium was cautiously acidified to pH 2–3, the precipitate formed was filtered, and the liquid phase was extracted with ethylacetate (3 5 250 ml). The organic layers were evaporated to dryness under reduced pressure leaving a white solid which was combined with the precipitate obtained by filtration, and suspended in dH$_2$O (250 ml). It was then filtered, washed with dH$_2$O (500 ml) and dried under high vacuum. The solid thus obtained was suspended in diethylether (250 ml) filtered, washed with diethylether (500 ml) and dried under high vacuum yielding FmocAla$_2$ (C$_{21}$H$_{22}$N$_2$O$_5$, 9.3 g, 77.5%) as a white solid. M.p.=192° C. Rf=0.35 (SiO$_2$, chloroform/MeOH/CH$_3$CO$_2$H 85/10/5). $^1$H NMR (DMF d$_7$)δ: 8.18 (d, $^3$J(H,H)=7.3 Hz, 1H, OCONH); 7.94 (d, $^3$J(H,H)=7.5 Hz, 2H, Ar); 7.77 (t, $^3$J(H,H)=7.5 Hz, 2H, Ar); 7.53 (d, $^3$J(H,H)=7.8 Hz, 1H, CONH); 7.44 (t, $^3$J(H,H)=7.5 Hz, 2H, Ar); 7.35 (t, $^3$J(H,H)=7.4 Hz, 2H, Ar); 4.45–4.20 (m, 5H, CHCH$_2$OCONH, CHCH$_3$); 1.37 (d, $^3$J(H,H)=7.2 Hz, 6H, CH$_3$).

$^{13}$C NMR (DMF d$_7$) δ: 174.8 (CO$_2$H); 173.2 (CONH); 156.7 (OCONH); 145.0, 144.9, 141.8, 128.4, 127.8, 126.2, 126.1, 120.8 (Ar); 67.0 (CH$_2$OCONH); 51.0 ( CHCH$_2$OCONH); 48.5, 47.7 (CHCH$_3$); 18.7, 17.8 (CH$_3$). FAB+MS (NBA): expected exact mass for (M+H$^+$)/z 383.1607, observed 383.1618.

Synthesis of Z-(L)Ala$_2$-(L)Tyr(Ot-Bu)OMe (26) Intermediate for (S8) as Illustrated in FIG. 4:

Compound 26: Compound 24 (2.35 g, 8 mMol; commercially available from Aldrich), the hydrochloride salt of 25 (2.3 g, 8 mMol; commercially available from Aldrich) and Et$_3$N (4.5 ml, 32 mMol) were stirred in DMF (80 ml) at 0° C. HBTU (6.0 g, 16 mMol) in DMF (80 ml) was added dropwise over 1 hour and the reaction mixture was stirred at 20° C. for 3 hours and stored at 0° C. overnight. dH$_2$O (20 ml) was added to destroy excess HBTU, and the solvent was evaporated to dryness under high vacuum. The solid thus obtained was chromatographed (SiO$_2$ flash, EA/DCM 0–50%). 26 was obtained as a white solid (C$_{21}$H$_{37}$N$_3$O$_7$, 3.75 g, 91.5%). M.p.=167° C. Rf=0.38 (SiO$_2$,' EA/DCM 50%). $^1$H NMR (CDCl$_3$) δ: 7.34 (m, 5H, Ph Z); 6.98 (d, $^3$J(H,H)=9 Hz, 2H, Tyr Ar); 6.89 (d, J(H,H)=8.5 Hz, 2H, Tyr Ar); 6.80 (d, $^3$J(H,H)=7.5 Hz, 1H, CONH); 6.73 (d, J(H, H)=7.5 Hz, 1H, CONH); 5.54 (d, $^3$J(H,H)=7.1 Hz, 1H, OCONH); 5.10 (d, $^3$J(H,H)=3.0 Hz, 2H, CH$_2$Ph Z); 4.78 (m, 1H, CHCH$_2$ Tyr); 4.49 (m, 1H, CHCH$_3$); 4.26 (m, 1H, C HCH$_3$); 3.65 (s, 3H, CO$_2$CH$_3$); 3.04 (d, $^3$J(H,H)=6.1 Hz, 2H, CHCH$_2$ Tyr), 1.40–1.20 (m, 15H, (CH$_3$)$_3$C and CH$_3$). $^{13}$C NMR (CDCl$_3$) δ: 172.1, 171.7, 171.5 (CO$_2$CH$_3$, CONH); 156.0 (OCONH); 154.5, 136.1, 130.4, 129.6, 128.5, 128.2, 128.1, 124.2 (Ar); 78.4 ((CH$_3$)$_3$C); 67.0 (CH$_2$OCONH); 53.4, 52.3, 48.9 (NHCHRCO); 50.5 (CO$_2$CH$_3$); 37.2 (CH CH$_2$ Tyr); 28.8 ((CH$_3$)$_3$C); 18.7, 18.3 (CH$_3$CH).

FAB+MS (NBA/CsI): expected exact mass for (M+Cs$^+$)/z 660.1686, observed 660.1664.

Synthesis of H$_2$N-(L)Ala$_2$-(L)Tyr(Ot-Bu)OMe (27) Intermediate for (S8) as Illustrated in FIG. 4:

Compound 27: Compound 26 (3.6 g, 7 mMol), Pd/C 10% (0.36 g, 10% w/w) were suspended in EtOH (175 ml) and placed under H$_2$ pressure (50 psi). The reaction mixture was vigorously shaken for 3 hours at 20° C. The suspension was then filtered on celite and the celite was washed with DCM (200 ml). The organic layers were combined and evaporated to dryness. 27 was obtained as a pale yellow oil (C$_{21}$H$_{31}$N$_3$O$_5$, 2.7 g, quantitative yield) and was used in the next step without further purification. Rf=0.28 (SiO$_2$, chloroform/MeOH/Et$_3$N 88/10/2) $^1$H NMR (CDCl$_3$) δ: 7.70 (d, $^3$J(H,H)=6.8 Hz, 1H, CONH); 7.00 (d, $^3$J(H,H)=8.4 Hz, 2H, Ar); 6.86 (m, 3H, Ar and CONH); 4.78 (m, 1H, CHCH$_2$ Tyr); 4.43 (m, 1H, CHCH$_3$); 3.67 (s, 3H, CO$_2$CH$_3$); 3.45 (brd, 1H, H$_2$NCHCH$_3$); 3.04 (m, 2H, CHCH$_2$ Tyr); 2.16 (brd, 2H, NH$_2$); 1.40–1.15 (m, 15H, (CH$_3$)$_3$C and CH$_3$). $^{13}$C NMR (CDCl$_3$) δ: 175.5, 171.9, 171.85 (CONH); 154.3, 130.7, 129.7, 124.1 (Ar); 78.4 ((CH$_3$)$_3$C); 53.3, 52.3, 48.3 (NHCHRCO); 50.4 (CO$_2$CH$_3$); 37.1 (CHCH$_2$ Tyr); 28.8 ((CH$_3$)$_3$C); 21.2, 17.5 (_H$_3$CH).

FAB+MS (NBA): expected exact mass for (M+H⁺)/z 394.2342, observed 394.2330.

Synthesis of Z-(L)Ala₄-(L)Tyr(Ot-Bu)OMe (28) Intermediate for (S8) as Illustrated in FIG. 4:

Compound 28: Compound 27 (2.6 g, 6.6 mMol), 24 (1.95 g, 6.6 mMol) and Et₃N (3.7 ml, 26.4 mMol) were stirred in DMF (60 ml) at 0° C. HBTU (4.9 g, 13.2 mMol) in DMF (60 ml) was added dropwise over 1 hour and the reaction mixture was stirred at 20° C. for 3 hours and stored at 4° C. overnight. dH₂O (20 ml) was added to destroy excess HBTU, and the solvent was evaporated to dryness under high vacuum. 28 was obtained as a white crystalline solid from boiling DCM (C₃₄H₄₇N₅O₉, 3.8 g, 87%). Decomposition point=232° C. ¹H NMR (DMSO d₆) δ: 8.24 (d, ³J(H,H)=7.4 Hz, 1H, CONH); 8.02 (d, ³J(H,H)=7.3 Hz, 1H, CONH); 7.92 (d, ³J(H,H)=7.5 Hz, 1H, CONH); 7.89 (d, ³J(H,H)=7.7 Hz, 1H, CONH); 7.49 (d, ³J(H,H)=7.4 Hz, 1H, CONH); 7.37–7.30 (m, 5H, Ph Z); 7.11 (d, ³J(H,H)=8.5 Hz, 2H, Tyr Ar); 6.86 (d, ³J(H,H)=8.4 Hz, 2H, Tyr Ar); 5.02 (s, 2H, PhC$\underline{H}_2$ Z); 4.42 (m, 1H, C$\underline{H}$CH₂ Tyr); 4.25 (m, 3H, C$\underline{H}$CH₃); 4.04 (m, 1H, C$\underline{H}$CH₃); 3.55 (s, 3H, CO₂CH₃); 2.93 (m, 2H, CHC$\underline{H}_2$ Tyr); 1.25 (s, 9H, (CH₃)₃C); 1.17 (m, 12H, CHC$\underline{H}_3$). ¹³C NMR (DMSO d₆) δ: 172.4, 172.2, 171.9, 171.6 ($\underline{C}$O₂CH₃ and CONH); 155.8 (OCONH); 153.7, 137.1, 131.6, 129.7, 128.4, 127.9, 127.8, 123.6 (Ar); 77.8 ((CH₃)₃$\underline{C}$); 65.4 ($\underline{C}$H₂OCONH); 53.7, 51.8, 48.1, 48.0, 47.8 (NH$\underline{C}$HRCO); 50.0 (CO₂$\underline{C}$H₃); 36.0 (CH$\underline{C}$H₂ Tyr); 28.6 ((CH₃)₃C); 18.3, 18.1 ($\underline{C}$H₃CH).

FAB+MS (NBA): expected exact mass for (M+H)/z 670.3452, observed 670.3483.

Synthesis of H₂N-(L)Ala₄-(L)Tyr(Ot-Bu)OMe (29) Intermediate for (S8) as Illustrated in FIG. 4:

Compound 29: Compound 28 (3.5 g, 5.2 mMol), Pd/C 10% (0.35 g, 10% w/w) were sonicated in EtOH/DMF 1/1 (175 ml) until complete dissolution of 28 (15–30 min) then placed under H₂ pressure (50 psi). The suspension was vigorously shaken for 5 hours at room temperature, filtered on celite, then the celite was washed with EtOH/DMF 1/1 (100 ml). The organic layers were evaporated to dryness under high vacuum. The solid obtained has a strong tendency to form gels in all common organic solvents. Pure compound 29 (C₂₆H₄₁N₅O₇, 2.7 g, quantitative yield) was obtained as a yellow foam from boiling CH₃CN. M.p.=198° C. (Rf=0.12 (SiO₂, CH₃CN). ¹H NMR (DMF d₇) δ: 8.29 (brd, 1H, CONH): 8.20 (d, ³J(H,H)=7.0 Hz, 1H, CONH); 8.15 (d, ³J(H,H)=7.6 Hz, 1H, CONH); 7.91 (d, ³J(H,H)=7.5 Hz, 1H, CONH); 7.20 (d, ³J(H,H)=8.5 Hz, 2H, Ar); 6.93 (d, ³J(H,H)=8.4 Hz, 2H, Ar); 4.57 (m, 1H, C$\underline{H}$CH₂ Tyr); 4.38 (m, 3H, C$\underline{H}$CH₃); 3.64 (s, 3H, CO₂CH₃); 3.57 (m, 1H, H₂C $\underline{H}$CH3); 3.04 (m, 2H, CHC$\underline{H}_2$ Tyr); 1.40–1.20 (m, 21H, (CH₃)₃C and CH₃). ¹³C NMR (DMF d₇) δ: 175.8, 173.3, 173.1, 172.7, 172.6 (CONH and $\underline{C}$O₂CH₃); 155.0, 132.6, 130.5, 124.5 (Ar); 78.4 ((CH₃)₃$\underline{C}$); 54.8, 51.2, 49.6, 49.5, 49.2 (NH$\underline{C}$HRCO); 52.2 (CO₂$\underline{C}$H₃); 37.2 (CH$\underline{C}$H₂ Tyr); 29.0 (($\underline{C}$H₃)₃C); 21.1, 18.6, 18.4, 18.1 ($\underline{C}$H₃CH). FAB+MS (NBA): expected exact mass for (M+H⁺)/z 536.3084, observed 536.3070.

Synthesis of Glutarate-(L)Ala₄-(L)Tyr(Ot-Bu)OMe (S8) as Illustrated in FIG. 4:

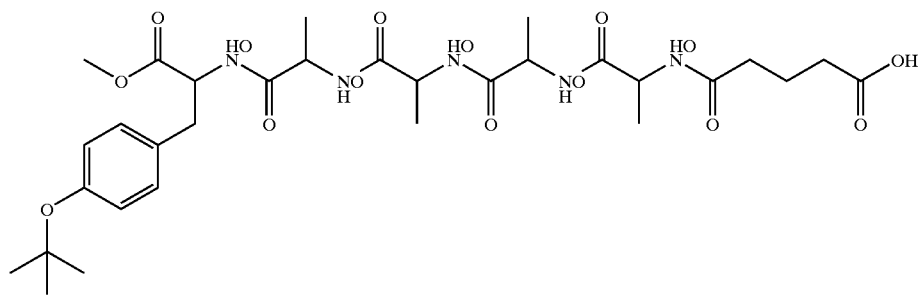

S8 = (L)MeO Tyr(Ot-Bu)-(L)Ala₄-Glutarate

Compound S8: Compound 29 (1 g, 1.9 mMol) and Et₃N (1.0 ml, 7.6 mMol) were stirred at 0° C. in DMF (100 ml). Glutaric anhydride (0.23 g, 1.9 mMol) in DMF (50 ml) was added dropwise over 45 min after which the temperature was raised to 20° C. for 3 h, then the reaction media was stored overnight at 4° C. The solvent was evaporated to dryness under high vacuum and the solid obtained was suspended in 0.1 M HCl (50 ml) and sonicated (10 min). The white precipitate was filtered and washed with 0.1 M HCl, dH₂O, DMF, dH₂O, and EtOH (100 ml each) and dried under high vacuum yielding S8 as a white powder (C₃₁H₄₇N₅O₁₀, 0.96 g, 78%). M.p.=263° C. ¹H NMR (DMSO ds) δ: 8.22 (d, ³J(H,H)=7.4 Hz, 1H, CONH); 8.04 (d, ³J(H,H)=6.6 Hz, 1H, CONH); 8.02 (d, ³J(H,H)=6.7 Hz, 1H, CONH); 7.88 (d, ³J(H,H)=6.7 Hz, 1H, CONH); 7.86 (d, ³J(H,H)=7.1 Hz, 1H, CONH); 7.10 (d, J(H,H)=8.4 Hz, 2H, Ar); 6.86 (d, ³J(H,H)=8.4 Hz, 2H, Ar); 4.41 (m, 1H, C$\underline{H}$CH₂ Tyr); 4.22 (m, 4H, C$\underline{H}$CH₃); 3.54 (s, 3H, CO₂CH₃); 2.92 (m, 2H, CHC$\underline{H}_2$ Tyr); 2.19 (t, ³J(H,H)=7.4 Hz, 2H, C$\underline{H}_2$CO₂H); 2.13 (t, ³J(H,H)=7.4 Hz, 2H, C$\underline{H}_2$CONH); 1.68 (m, 2H, HO₂CCH₂C$\underline{H}_2$) 125 (s, 9H, (CH₃)₃C); 1.22–1.10 (m, 12H, CH₃). ¹³C NMR (DMF d₇) δ: 174.9, 174.3, 173.7, 173.6, 173.0, 172.7, 172.65 (CONH, CO₂H, $\underline{C}$O₂CH₃); 155.0, 132.7, 130.6, 124.5 (Ar); 78.6 ((CH₃)₃$\underline{C}$); 54.8, 50.6, 50.4, 49.8, 49.4 (NH$\underline{C}$HRCO); 52.2 (CO₂$\underline{C}$H₃); 37.3 (CH$\underline{C}$H₂ Tyr); 35.1, 33.8 (HO₂C$\underline{C}$H₂CH₂$\underline{C}$H₂CONH); 29.0 (($\underline{C}$H₃)₃C); 21.5, 18.2, 17.8, 18.7 (HO₂CCH₂$\underline{C}$H₂ CH$\underline{C}$H₃). FAB+MS (NBA/CsI): expected exact mass for (M+Cs⁺)/z 782.2377, observed 782.2397; 914 (M−H++2Cs⁺)/z.

Early Embodiments of the Encoded Reaction Cassette: the Matrix:

In early attempts to implement this technology we encountered a variety of problems. First, certain matrix materials, like CPG (Controlled Pore Glass), were labile and liberated the polynucleotide-substrate hybrid leading to an undesired background reaction. We presumed that cleavage of a bond between the solid support and the first linker was responsible for this problem. In addition to the problem with its lability, CPG possesses free hydroxyl groups on which the polynucleotide chain can be grown during polynucleotide synthesis (25), leading to unwanted labile bonds. A second difficulty was that enzymatic cleavage of the cassette was slow and incomplete (data not shown) because of steric hindrance of the substrate by the matrix and/or the polynucleotide. For this reason we had to extend the length of the linkers either between the solid support and the substrate and/or the substrate and the polynucleotide. For our purposes TentaGel was found to have much better mechanical and chemical properties. Furthermore, it possesses a long polyoxyethylene arm which attenuates the hindrance problem. Finally, the synthesis had to be simple so that the cassette can be easily prepared in a short time. All these considerations led to the strategy depicted in scheme 1.

TentaGel is a tentacle copolymer of PEG (polyethylene glycol), and PS (polystyrene). It has been used successfully in solid phase peptide synthesis, e.g., B. G. de la Torre, B. G. et al. *Tetrahedron Lett.* (1994): vol. 35, pages 2733–2736; J. Haralambidis et al., *Tetrahedron Lett.* (1987):

SCHEME 1

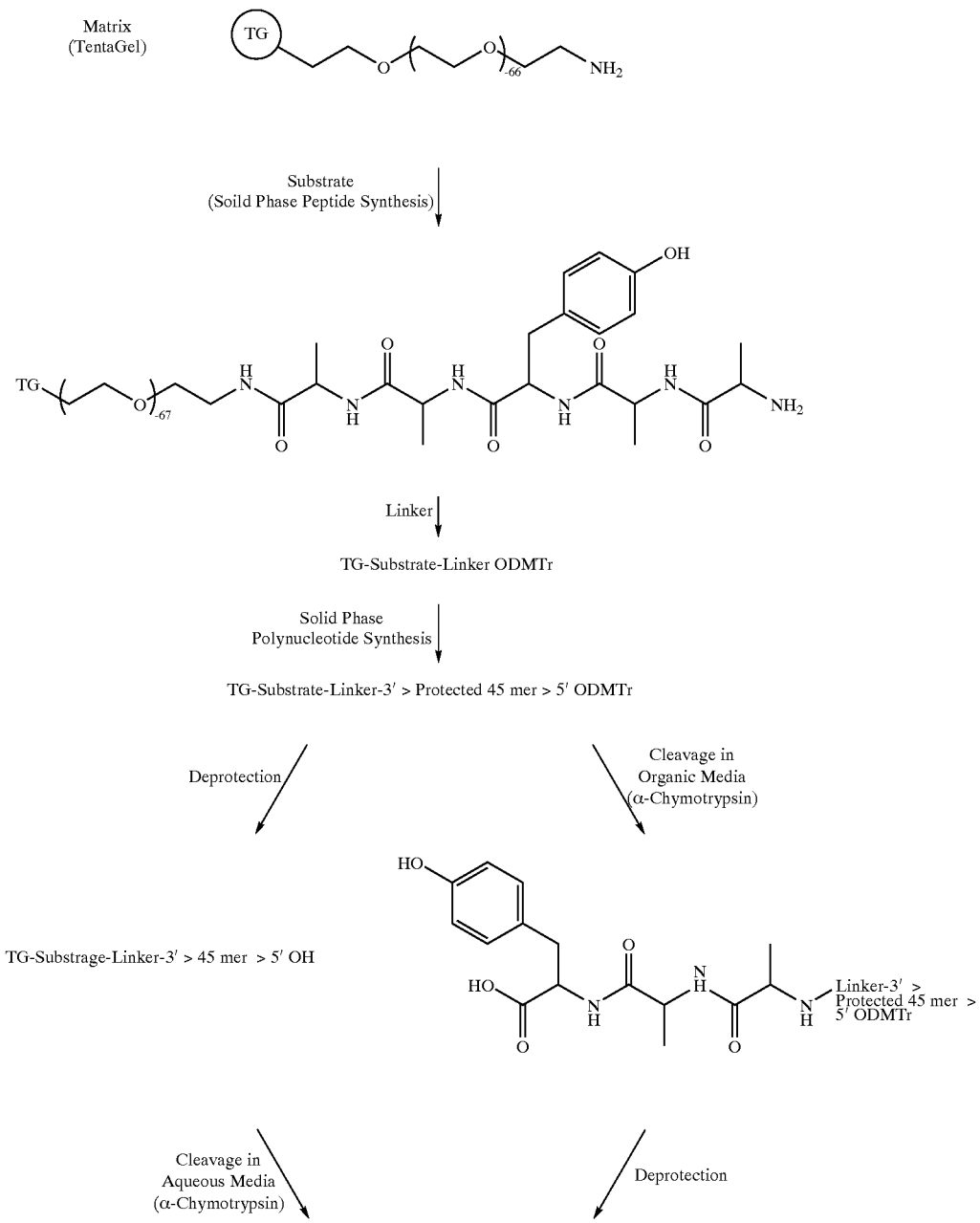

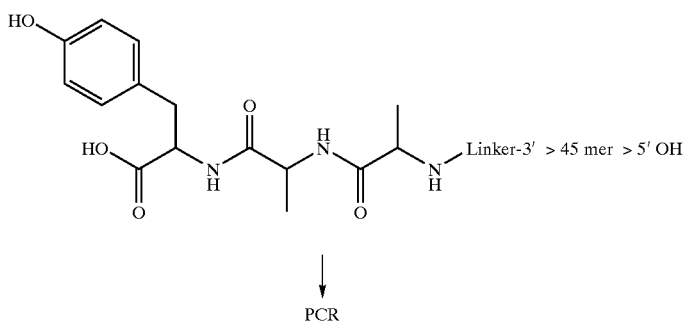

↓
PCR vol. 26, pages 5199–5202; and G. Barany, et al. in *Peptides: Proceedings of the Twelfth American Peptide Symposium* (1992): Escon, Leiden, page 604. It has been used successfully in solid phase DNA synthesis, e.g., H. Gao et al. *Tetrahedron Lett.* (1991): vol. 32, pages 5477–5480 and P. Wright et al. *Tetrahedron Lett.* (1993): vol. 34, pages 3373–3376. TentaGel has also been shown to be compatible with biocatalysts, e.g., L., Meldal et al. *J. Chem. Soc., Chem. Commun.* (1994), p. 1849. It is stable to extremes of pH, and can be used in a variety of solvents. Its high swelling properties (4–7 times) in all usual solvents is an additional feature that makes it attractive for reactions involving biocatalysis. This polymer has the same mobility and dynamics as polyethylene glycol which has been used as a soluble support for oligonucleotide synthesis, e.g., E. Bayer, *Angew. Chem., Intl. Ed. Engl.* (1991): vol. 32, pages 5477–5480. It has a high diffusion coefficient, sorption, and mechanical stability. The reaction kinetics are of the same order as in solution because the functional groups are completely solvated (supra). Since the polyethylene glycol part of the resin (70–80% w/w), dominates its physico-chemical behavior the substrate-polynucleotide hybrid grown on it will be solubilized in organic or aqueous solutions. Finally, this matrix is commercially available with different functionalities (OH, $NH_2$, SH, $CO_2H$, CHO, Br), which will facilitate the introduction of different types of substrates.

Synthesis of the Substrate Portion of the Cassette:

The catalyst chosen to study our cassette methodology had to be chemically and physically well defined. α-chymotrypsin seemed to be an ideal enzyme for this purpose. The substrate portion of the cassette was L-Ala$_2$—L-Tyr—L-Ala, which is known to be the best substrate for α-chymotrypsin, e.g., W. K. Baumann et al., *Eur. J. Biochem.* (1973): vol. 39, 381–391. The choice of this substrate was dictated by the fact that our goal in these initial studies was to explore the lower limit of the sensitivity of the system.

It was not necessary to introduce a spacer between the solid support and the substrate since the TentaGel matrix is endowed with an extended polyethylene glycol arm bearing a terminal functional group that allows the direct attachment of the cassette substrate (Scheme 1). The loading of the matrix is about 280 millimoles/gram. In order to avoid the generation of hindered sites, we functionalized only the most exposed ones (40–60 millimoles/gram) by adding a large excess of matrix in the first step of the synthesis and capping the unreacted groups.

We anticipated that the spacing between the substrate and the DNA tag was a critical design feature of the cassette and, thus, four different linkers were prepared (FIG. 15). Linker L-I looses slowly the Fmoc (9-fluorenylmethoxycarbonyl) protecting group inducing the formation of a side product that is not practical to separate from the pure compound. Thus, we prepared the more stable derivative L-II which has a CBZ (benzyloxycarbonyl) protecting group. Unfortunately, the acetoxy group in both L-I and L-II was found to be labile under the strongly acidic conditions required for the deprotection of the substrate ($CF_3CO_2H$/ethandithiol 95%, 2 hours). Accordingly, it is preferable to prepare a longer version of L-I, L-III which does not have the labile acetoxy moiety. However, L-III did not couple efficiently with peptide on the resin. Instead, the free amino group (matrix-peptide) reacted irreversibly with the Fmoc of the linker, e.g., G. B. Fields et al. *Int. J. Pep. Prot. Res.* (1990)L vol. 35, 161–214. Accordingly, these results teach that L-IV is the preferred linkage agent. All data reported herein employs cassettes with this linkage agent. Since only the above three linkage agents have been tested to date, there is a possibility that other as yet untested linker appendages may prove superior.

The peptide sequence selected as an exemplary substrate requires a deprotection step on the Tyrosine-O-t-Bu with $CF_3CO_2H$/ethandithiol, 95% for 2 hours. Since this deprotection can not be performed after the polynucleotide synthesis (concentrated acid leads to many side reactions on the polynucleotide), it was necessary to change the Tyrosine protecting group from a t-Bu to a base labile protecting group which can be removed at the same time as the deprotection of the DNA. Scheme 2 illustrates a pathway employed for protecting group exchange and for the introduction of the linker. Aside from its utility for the present experiment, this synthesis shows that the system can be readily transformed and modified chemically so as to be compatible with a variety of substrates.

SCHEME 2

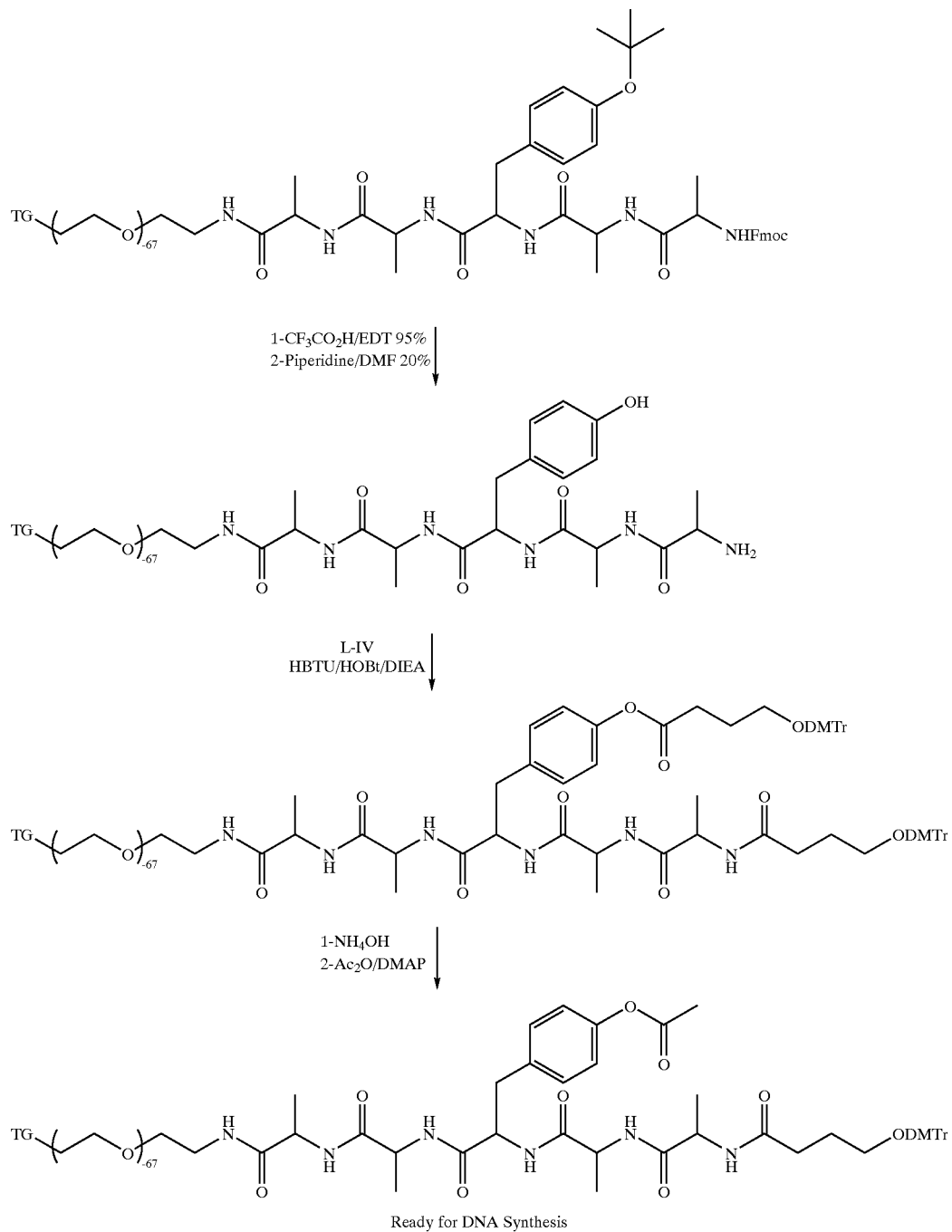

Ready for DNA Synthesis

Figure 16:
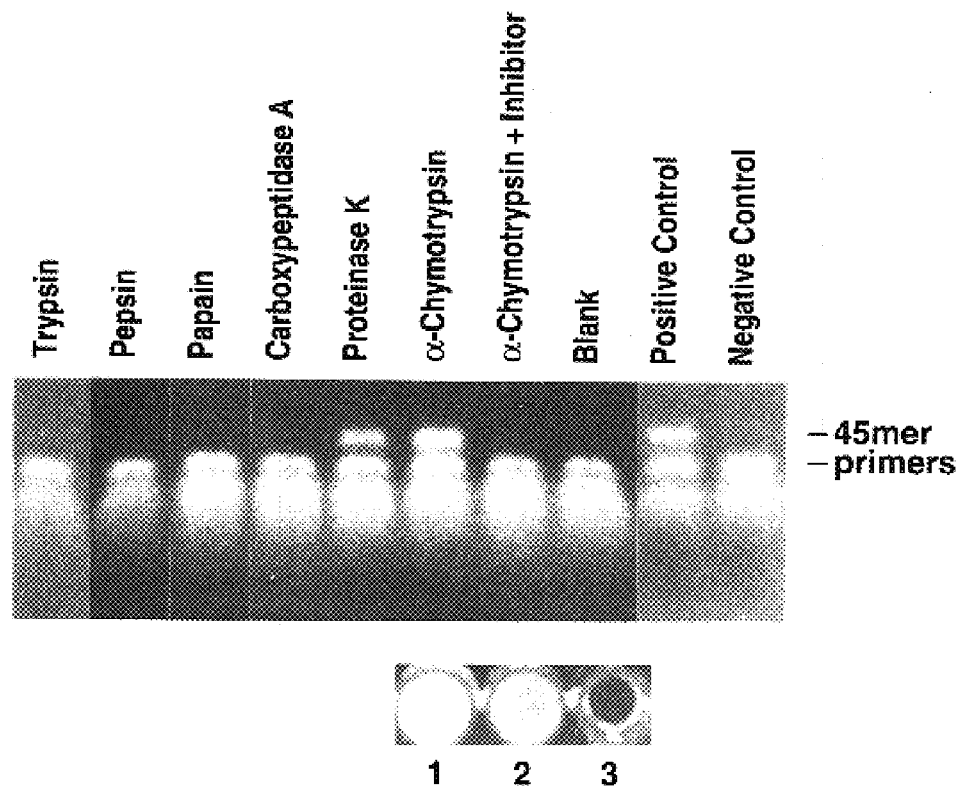
FIG. 16 illustrates the reaction specificity of a peptide reaction cassette with respect to indicated proteolytic enzymes.

Synthesis of the Polynucleotide Portion of the Cassette. The polynucleotide sequence is shown in FIG. 16. It possesses two primer sequences and one encoding sequence which identifies the substrate which in this case is a pentapeptide where each amino acid is arbitrarily assigned a triplet nucleotide sequence. Obviously, any nucleotide sequence may be used to encode the nature of the substrate and the choice of the nature of the code will depend primarily on the number and complexity of test substrates.

Standard phosphoramidite methodology using CPG solid support, on a 394 Applied Biosystem DNA Synthesizer, was not efficient with the TentaGel matrix, e.g. M. J. Gait, Ed. (1990) *Oligonucleotide Synthesis, a Practicable Approach* (Oxford University Press, New York). The yield per step dropped from ~98% to ~85%. After 45 steps, the overall yield with the CPG was ~40% and only ~0.07% with the TentaGel. Modification of the classical procedure was required. After many trials, three major modifications of the procedure (see materials and methods) were found to increase the yield per step from ~85% to ~97%, corresponding to an increase in the overall yield from ~0.07% to ~25%. The polynucleotide encoded peptide thus obtained was submitted to concentrated ammonia to deprotect the polynucleotide and the peptide, followed by 3% trichloroacetic acid in dichloromethane treatment to remove the dimethoxytrityl protecting group.

Figure 17:
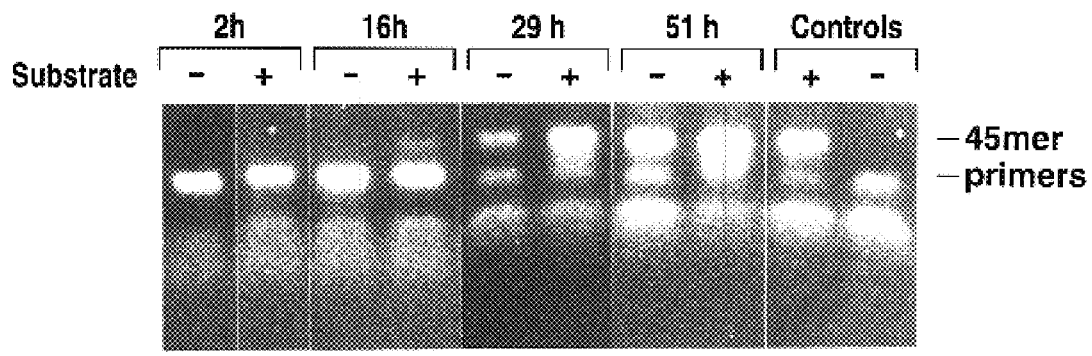
FIG. 17 illustrates the reaction sensitivity of the peptide reaction cassette of FIG. 16 as a function of time.

Reaction Specificity. The cassette was submitted to enzyme cleavage and the results after the amplification by PCR of the liberated polynucleotide are illustrated in FIG. 17.

Lanes 1–8 show the results after incubation at 20° C. for 30 minutes with trypsin, pepsin, papain, carboxypeptidase A, proteinase K, α-chymotrypsin, α-chymotrypsin+ Bowman-Birk inhibitor, and no enzyme, e.g., Y. Birk, Y. *Int. J. Peptide Protein Res.* (1985): vol. 25, pages 113–131. Lane 9 corresponds to the positive control and lane 10 to the negative control.

The data in lane 6 show that in the presence of α-chymotrypsin a band corresponding to 45 nucleotides is present, indicating a net cleavage of the substrate by this enzyme. This interpretation is further supported by the control experiments. When the cassette is incubated with trypsin, pepsin, papain, or carboxypeptidase A, no band could be detected on the agarose gel which is in agreement with the specificity of these enzymes. When the Bowman-Birk inhibitor is added to α-chymotrypsin (lane 7), no cleavage is detected. As expected, in the presence of proteinase K a band is detected indicating a net cleavage by this enzyme. The intensity of the band indicates that the cleavage by proteinase K is weaker than that accomplished by α-chymotrypsin. This result is in agreement with the fact that α-chymotrypsin is specific for the substrate used in this study. In the absence of any enzyme (lane 8) no cleavage is detected after 30 minutes.

Under the reaction conditions used in this study, the enzymatic activity of 1 picomole of α-chymotrypsin was readily detected. One should be able to improve the sensitivity of detection since the substrate concentration (29.5 mM) used in our experiment was well below saturation (32). Additionally, preliminary experiments have shown that a longer linker between the substrate and the polynucleotide enhance the accessibility of the enzyme to the substrate (data not shown).

An alternative to analyzing the PCR products on agarose gel, which can become laborious when libraries of catalysts are being screened, one can simply add to the reaction mixture a fluorescent probe that undergoes fluorescence enhancement upon intercalation into the DNA. The insert in FIG. 17 shows a photograph taken under UV light (254 nm) of the reaction media in the presence of the YOYO-1 The first well corresponds to the experiment in lane 6, the second well to the experiment in lane 8, and the third to the probe in buffered solution without any additives. The greatest fluorescence enhancement is in the first well which contains the amplified DNA. The second well shows a background fluorescence resulting from the interaction of the probe with the primers. As expected, the third well does not show any detectable fluorescence. Another advantage of the YOYO-1 probe is that the amount of the PCR product (which should be directly related to the efficiency of the enzyme cleavage) can be quantified, e.g., M. Ogura et al., *Biotechniques* (1994): vol. 16, pages 1032–1033.

Reaction Sensitivity. It was interesting to note that after 24 hours, in the absence of α-chymotrypsin, a band corresponding to the DNA 45mer was detected (data not shown). This background reaction can be due to bond solvolysis anywhere between the solid support and the first bases of the polynucleotide, or simply to a leakage from the matrix. In an attempt to define the cleavage site(s) we prepared the same cassette lacking the substrate unit (where the polynucleotide is directly linked to the matrix via a mixed phosphodiester bond). When this matrix and the standard cassette are incubated separately without any catalyst, one can detect a background reaction after 16 hours. The ease of detection of this uncatalyzed reaction increases between 29 hours and 51 hours.

If this uncatalyzed reaction originated from leakage from the matrix or solvolysis of a phosphodiester bond, the 45mer DNA would have been detected at the same time irrespective of whether the cassette contained a substrate unit. The fact that detectable cleavage after 16 hours is limited to cassettes containing the peptide substrate indicates that bond solvolysis occurs in the substrate sequence, most likely at a peptide bond. After 16 hours when background cleavage of the peptide bond is observed, solvolysis of the phosphodiester bond is not detected. However, by 29 hours solvolysis of the phosphodiester bond is detected.

Assuming that the rate constant for a peptide bond hydrolysis is $~3\times10^{-9}$ s$^{-1}$ ($t_{1/2}$ ~7 years), at a cassette concentration of 29.5 mM the velocity for peptide bond hydrolysis is $~9\times10^{-14}$ M/s, e.g., D. Kahn & W. C. Still, *J. Am. Chem. Soc.* (1988): vol. 110, pages 7529–7534. After 15 hours one would expect to have ~5 nanomoles of free polynucleotide in solution. This amount is known to be readily detectable by the PCR. Since the rate constant for phosphodiester bond hydrolysis is much slower ($5.7\times10^{-11}$ s$^{-1}$) than that of peptide bond hydrolysis, the background for the cassette lacking the substrate unit will be detected only after longer incubation times, e.g., E. H. Serpersu et al. *Biochemistry* (1987): vol. 26, pages 1289–1300.

Practicality of the Encoded Cassette System. It herein disclosed that the cassette system works reproducibly, and that the entire cassette can be assembled in less than 48 hours using conventional synthetic chemistry. Because of the simplicity and versatility of our methodology, analysis of a large number of potential catalysts can be carried out in less than 4 hours. Although, the current limit of detection is about ~1 picomoles, the sensitivity and efficiency of this system can be readily improved. These improvements may be achieved either by increasing the concentration of the substrate, and/or its loading on the solid support and/or introducing longer linkers between the substrate and the polynucleotide.

The system is not limited to transformations in which bond cleavage or bond formation is the initial event. The only requirement is that the chemical transformation make a bond labile to other reagents. For example, in the search for dihydroxylation catalysts, an olefin can be used as a substrate because when it is dihydroxylated it can be selectively cleaved by periodate. Additionally, one can envision systems in which the transformation modifies the cassette such that it now becomes a substrate for a known enzyme, e.g., K. Morikawa et al., *J. Am. Chem. Soc.* (1993): vol. 115, pages 8463–8464.

Finally, even using PCR conditions that are not yet optimized, it is herein demonstrated that one is able to detect in a matter of hours uncatalyzed chemical reactions with half-lives of years. This demonstrates that essentially any catalytic bond cleavage or formation event can in principle be readily detected in a very short time. The method should be applicable to detection of events that are of low efficiency either because the enzyme is poor or, more importantly, because the catalyst is only one member of a large library and is, thus, present in low concentration.

Materials and Methods

The chemicals were purchased from Novabiochem and Aldrich for peptide synthesis, from Millipore for DNA synthesis, and from Promega for the PCR experiments. The YOYO-1 probe was purchased from Molecular Probes Inc. The solvents were purchased from Fisher or Baxter (water content<0.001%). For synthesis of the linkers, the chemicals were purchased from Aldrich, and were used without any further purification.

Substrate Synthesis. TentaGel is commercially available from Novabiochem or Rapp Polymere (Germany). The peptide was assembled according to standard Fmoc methodology, e.g., A. Aherton & R. C. Sheppard, *Solid Phase Peptide Synthesis: A Practicable Approach* (1989): Oxford University Press. In a typical procedure, 3 equivalents of the coupling reagent for amide bond formation, 2-(1H-Benzotriazole-1-yl)-1,1,3,3 tetramethyluroniun Hexafluoro-phosphate (HBTU), 3 equivalents of N-Hydroxybenzotriazole (HOBt), 6 equivalents of N,N-diisopropyl-ethylamine (DIEA), and 3 equivalents of the N-α(9-fluorenylmethoxycabonyl)-amino acid (Fmoc-aa) are added in dimethylacetamide to the resin swollen in dichloromethane (DCM). The coupling was completed in less than an hour as judged by the Kaiser test, e.g., E. Kaiser et al. *Analyt. Biochem.* (1970): vol. 34, page 595 and V. K. Sarin et al. *Analyt. Biochem.* (1981): vol. 117, 147. After each step the resin was washed with N,N-dimethyformamide, methanol, and DCM. The Fmoc protecting group was removed upon treatment with 20% piperidine in N,N-dimethylformamide (2×10 minutes). The yield of ma each step was determined by the titration of the Fmoc group from a small sample, e.g., A. Atherton, A. & R. C. Sheppard, R. C., *Solid Phase Peptide Synthesis: A Practicable Approach* (1989): Oxford University Press, p. 107. To have a final loading of 40–60 millimoles/gram, the first step of the synthesis was performed with four fold excess of solid support to Fmoc-aa. After all the final washings, the unreacted amino groups were capped (0.25 volume of acetic anhydride 4.23 M in 2,6-lutidine; 0.75 volume of N,N-dimethylaminopyridine, 0.53 M in THF, 2×10 minutes). The overall yield for peptide synthesis was ~98%.

The t-Butyl protecting group for the hydroxyl moiety on tyrosine was removed by treatment with $CF_3CO_2H$/ethandithiol 95% for 2 hours, followed by extensive washing with DCM, methanol, and N,N-dimethylformamide. The Fmoc protecting group was removed before coupling to the linker (see scheme II). The matrix containing Tyrosine-O-L-IV was converted to Tyrosine-O-acetyl after selective deprotection of the phenolic ring (concentrated $NH_4OH$, 3 hours) and capping (0.25 volume of acetic anhydride, 4.23 M in 2,6-lutidine, 0.75 volume of N,N-dimethylaminopyridine, 0.53 M in THF, 30 min). The yield after each step was determined by the dimethoxytrityl cation assay, e.g., M. J. Gait, *Oligonucleotide Synthesis: A Practicable Approach* (1990): Oxford University Press, p. 48.

Linker L-IV was prepared in one step from the sodium salt of 4-hydroxybutyrate and dimethoxytrityl chloride in pyridine, e.g., H. Schaller et al., *J. Am. Chem. Soc.* (1963): vol. 85, pages 3821–3827.

DNA synthesis. DNA synthesis was carried out on a 394 Applied Biosystem DNA Synthesizer. The standard 1 millimole cycle was modified as follows 1) All washing steps 3, 59, 61, 66, 77, and 94 were prolonged to 30 seconds. The use of longer or shorter times decreased the yield. 2) The incubation time with phosphoramidite and tetrazole (step 45) was prolonged from 25 seconds to 120 seconds. 3) The concentration of the phosphoramidites was increased from 0.1 M to 0.2 M. The bases were deprotected upon treatment with concentrated $NH_4OH$ for 20 hours at 55° C. The dimethoxytrityl group is removed upon treatment with 3% trichloroacetic acid in DCM (5 minutes), followed by extensive washing with DCM, tetrahydrofuran, methanol, tris-HCl buffer (20 millimolar, pH 8, NaCl 160 millimolar), and $dH_2O$ (deionized water). After this step, the cassette is ready for use.

Enzymatic Cleavage and inhibition Experiments. The cassette (1 mg, 5.9 millimoles/gram) was suspended in 20 ml tris-HCl buffer (20 millimolar, pH 8, NaCl 160 millimolar) and 170 ml $dH_2O$. 0.85 mMol of trypsin, pepsin, papain, carboxypeptidase A, O-chymotrypsin, or α-chymotrypsin+1 mg Bowman-Birk inhibitor (19) in 10 ml $dH_2O$ was added to the reaction media, and the mixture was shaken at 20° C. Supernatant fluids (18.7 ml) were taken after 30 minutes and were submitted to the PCR.

PCR Experiments. Aliquots (18.7 ml) from the reaction mixture were mixed with the PCR components ($MgCl_2$ 2.5 millimolar, 1.2 ml; Taq buffer, 2 ml; deoxynucleotide triphosphates 2.5 millimolar, 1.6 milliliters; primers 100 picomoles/milliliter, 1 milliliter). Taq polymerase (2.5 U, 0.5 ml), was added just before starting the first PCR cycle. A positive control (PCR components only) was run with $dH_2O$ containing 1 picomole of the polynucleotide sequence used in this study. A negative control was run under the same conditions without the polynucleotide sequence. The PCR was run on a Perkin-Elmer-Cetus 9600 instrument with the following cycle program: denaturation 94° C., 30 seconds; annealing 55° C., 30 seconds; extension 72° C., 30 seconds. After 35 cycles the results were analyzed on agarose gels (1% Gibco-BRL, 2% Nu Sieve GTG, TBE 1×, 103 millivolts).

Fluorescence Assay. After the PCR, the reaction supernatant (25 ml) was transferred to a 96-well ELISA plate and diluted to 250 ml with $dH_2O$ (175 ml) and methanol (50 ml). The probe (1 ml, YOYO-1) was added to this media, and the results were analyzed under UV light (254 nm).

Uncatalyzed Reactions. The cassette lacking the substrate unit was prepared as follows: TentaGel bearing a hydroxyl group functionality (1 g) was shaken with dimethoxytrityl chloride (10 eq, 85 mg) in pyridine (4 ml) at room temperature for 3 days. Titration of the dimethoxytrityl group showed a loading of 32 millimole/gram. The unreacted hydroxyl groups were acetylated (0.25 volume of acetic anhydride, 4.23 M in 2,6-lutidine, 0.75 volume of N,N-dimethylaminopyridine, 0.53 M in THF; 30 minutes). DNA synthesis was performed on this matrix following the procedure described above.

The cassette lacking the substrate (0.5 mg, 12.2 millimoles/gram) and the cassette with the substrate unit (1 mg, 6.2 millimoles/gram) were suspended separately in 20 ml of tris-HCl buffer (20 millimolar, pH 8, NaCl 160 millimolar) and 180 milliliter of $dH_2O$. The mixtures were shaken at 20° C. and aliquots (18.7 ml) taken after 2 hours, 16 hours, 29 hours, and 51 hours were subjected to the PCR.

What is claimed is:

1. A process for identifying the presence of a proteolytic cleavage activity within a sample, the process comprising the following steps:

Step A: admixing the sample, potentially including a proteolytic enzyme or antibody, with an encoded reaction cassette under conditions for enabling the cleavage activity, if present within the sample, to cleave the encoded reaction cassette, the encoded reaction cassette including a solid phase matrix, a peptide substrate susceptible to cleavage by means of the proteolytic cleavage activity, and a polynucleotide having an encoding sequence capable of amplification by PCR and of detection after amplification for identifying the presence of the proteolytic cleavage activity, the solid phase matrix being linked to the polynucleotide by the peptide substrate, said cleavage of the encoded reaction cassette resulting in the formation of a soluble phase cleavage product, the soluble phase cleavage product including the polynucleotide and a cleaved portion of the peptide substrate; then Step B: isolating the soluble phase cleavage product produced in said Step A, if any; then Step C: amplifying, by PCR, the encoding sequence of the soluble phase cleavage product isolated in said Step B; then Step D: detecting the amplified encoding sequence of the soluble phase cleavage product of said Step C, if any, for identifying the presence of the proteolytic cleavage activity within the sample.

* * * * *

SEQUENCE LISTING

<160> NUMBER OF SEQ ID NOS: 14

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: substrate

<400> SEQUENCE: 1

Gly Gly Phe Gly
 1

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: substrate

<400> SEQUENCE: 2

Ala Ala Phe Ala Ala
 1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: substrate

<400> SEQUENCE: 3

Ala Ala Tyr Ala Ala
 1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: substrate
<220> FEATURE:
<221> NAME/KEY: MOD_RES
<222> LOCATION: (5)
<223> OTHER INFORMATION: Xaa = Alanine-Glutarate

<400> SEQUENCE: 4

Ala Ala Tyr Ala Xaa
 1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: substrate

<400> SEQUENCE: 5

Ala Ala Ala Ala Tyr Ala Ala Ala Ala
 1               5

<210> SEQ ID NO 6
<211> LENGTH: 6
<212> TYPE: PRT
<213> ORGANISM: Artificial Sequence
<220> FEATURE:

-continued

```
<223> OTHER INFORMATION: Description of Artificial Sequence:  substrate
<220> FEATURE:
<221> NAME/KEY: MOD_RES
<222> LOCATION: (1)
<223> OTHER INFORMATION: Xaa = Methylated Tyrosine-o-t-Butyl
<220> FEATURE:
<221> NAME/KEY: MOD_RES
<222> LOCATION: (6)
<223> OTHER INFORMATION: Xaa = Alanine-Glutarate

<400> SEQUENCE: 6

Xaa Ala Ala Ala Ala Xaa
 1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence:  substrate
<220> FEATURE:
<221> NAME/KEY: MOD_RES
<222> LOCATION: (3)
<223> OTHER INFORMATION: Xaa = Tyrosine-o-t-Butyl

<400> SEQUENCE: 7

Ala Ala Xaa Ala Ala
 1               5

<210> SEQ ID NO 8
<211> LENGTH: 45
<212> TYPE: DNA
<213> ORGANISM: Artificial Sequence
<220> FEATURE:
<223> OTHER INFORMATION: Description of Artificial Sequence:  template

<400> SEQUENCE: 8
gattcttatc ccgggctgat cgtcctcgag ggaacccttc atcga            45

<210> SEQ ID NO 9
<211> LENGTH: 45
<212> TYPE: DNA
<213> ORGANISM: Artificial Sequence
<220> FEATURE:
<223> OTHER INFORMATION: Description of Artificial Sequence:  substrate

<400> SEQUENCE: 9
agctacttcc caagggagct gctgctagtc gggccctatt cttag            45

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence:  template

<400> SEQUENCE: 10
ctaagaatag ggcccgacta gcagcagctc ccttgggaag tagct            45

<210> SEQ ID NO 11
<211> LENGTH: 45
<212> TYPE: DNA
<213> ORGANISM: Artificial Sequence
<220> FEATURE:
<223> OTHER INFORMATION: Description of Artificial Sequence:  template

<400> SEQUENCE: 11
ggcggcttcc caagggagct gctgctagtc tattcttagg ggccc            45
```

```
<210> SEQ ID NO 12
<211> LENGTH: 45
<212> TYPE: DNA
<213> ORGANISM: Artificial Sequence
<220> FEATURE:
<223> OTHER INFORMATION: Description of Artificial Sequence: template

<400> SEQUENCE: 12
ggcggcttcc caagggagct gctgctagtc taggcgtagg ggccc            45

<210> SEQ ID NO 13
<211> LENGTH: 45
<212> TYPE: DNA
<213> ORGANISM: Artificial Sequence
<220> FEATURE:
<223> OTHER INFORMATION: Description of Artificial Sequence: template

<400> SEQUENCE: 13
ggcgacgtga tgggcaattt gatgatagac taggcggagg cgagg            45

<210> SEQ ID NO 14
<211> LENGTH: 45
<212> TYPE: DNA
<213> ORGANISM: Artificial Sequence
<220> FEATURE:
<223> OTHER INFORMATION: Description of Artificial Sequence: template

<400> SEQUENCE: 14
cgcagggtga gtaaggcagc atacgcagca atagtggacg gagcg            45
```